US005451500A

United States Patent [19]

Stapleton

[11] Patent Number: 5,451,500
[45] Date of Patent: * Sep. 19, 1995

[54] DEVICE FOR PROCESSING BIOLOGICAL SPECIMENS FOR ANALYSIS OF NUCLEIC ACIDS

[75] Inventor: Marilyn J. Stapleton, Durham, N.C.

[73] Assignee: Gene Tec Corporation, Durham, N.C.

[*] Notice: The portion of the term of this patent subsequent to Jan. 25, 2011 has been disclaimed.

[21] Appl. No.: 836,348
[22] PCT Filed: Nov. 16, 1990
[86] PCT No.: PCT/US90/06768
§ 371 Date: Mar. 3, 1992
§ 102(e) Date: Mar. 3, 1992
[87] PCT Pub. No.: WO91/07486
PCT Pub. Date: May 30, 1991
[51] Int. Cl.$^6$ ............................................... C12Q 1/70
[52] U.S. Cl. ........................................ 435/6; 439/294; 439/290; 439/289; 935/87
[58] Field of Search ................. 435/6, 290, 294, 289; 935/87

[56] References Cited

U.S. PATENT DOCUMENTS

| | | | |
|---|---|---|---|
| 3,762,877 | 10/1973 | Rains et al. | 23/230 B |
| 3,915,647 | 10/1975 | Wright et al. | 23/153 |
| 4,260,392 | 4/1984 | Lee | 23/230 R |
| 4,632,808 | 12/1986 | Yamamoto et al. | 422/72 |
| 4,683,195 | 8/1987 | Mullis | 435/91 |
| 4,683,202 | 7/1987 | Mullis et al. | 435/6 |
| 4,695,548 | 9/1987 | Cantor et al. | 435/179 |
| 4,775,635 | 10/1988 | Ebersole et al. | 436/501 |
| 4,861,712 | 8/1989 | Bartl et al. | 435/13 |
| 5,021,335 | 5/1991 | Tecott et al. | 435/6 |
| 5,112,736 | 5/1292 | Caldwell et al. | 435/6 |

FOREIGN PATENT DOCUMENTS

WO89/05457 11/1989 WIPO .

OTHER PUBLICATIONS

Wu et al., Genomics, 4:450–469, 1989.

(List continued on next page.)

Primary Examiner—Margaret Parr
Assistant Examiner—Scott W. Houtteman
Attorney, Agent, or Firm—Olive & Olive

[57] ABSTRACT

A system is provided for the automated detection of target nucleic acid sequences in which multiple biological samples are individually incorporated into matrices within carriers in a two-dimensional format. The matrix carrier is an inexpensive, disposable unit that represents a closed system separating the specimens. The system integrates sample preparation within the matrix and facilitates biochemical reactions, addition of reagents and washes, removal of waste fluids, temperature control and the automated processing thereof. The carriers are processed in stepwise treatments that expose, amplify, and detect the presence or absence of specific genetic entities in each sample. The nucleic acids or other desired biological components held within the matrices are treated by one or more of the techniques such as amplification, electrophoresis, analyte-receptor binding or hybridization as selected for the desired analysis. Different types of carriers are used for different kinds of diagnostic tests or test panels. Different primer and polymerase molecules may be used to replicate the target sequences of nucleic acids in the sample. The system also includes a heating and a passive cooling system that will provide rapid thermal cycling in a two-dimensional format for denaturation and amplification protocols so requiring them, or maintain constant temperatures for isothermal amplification and hybridization protocols. The system is adaptable to a variety of non-isotopic labels. The two-dimensional format lends itself to digitizing signals in a two-dimensional array for image analysis. Microscopic interpretation is possible with or without image analysis.

5 Claims, 9 Drawing Sheets

OTHER PUBLICATIONS

Borst, P., A. M. Van Der Bliek, T. Van Der Velde—Koerts and E. Has. 1987. Structure of amplified DNA, analyzed by pulsed field gradient gel electrophoresis. J. Cellular Biochem. 34:247–258. (Aug. 1987).

Kwoh, D. Y., G. R. Davis, K. M. Whitfield, H. L. Chappelle, L. J. DiMichele and T. R. Gingeras. 1987. Transcription—based amplification system and detection of amplified HIV-1 using a bead-based sandwich hybridization format. Reprint. Personal Communication.

Ou, C. Y., S. Kwok, S. Mitchell, D. Mack, J. Sninsky, J. Krebs, P. Feorino, D. Warfield, G. Schochetman. 1988. DNA amplification for direct detection of HIV-1 in DNA of peripheral blood mononuclear cells. Sci. 239:295–297. (Jan. 15, 1988).

Saiki, R. K., D. H. Gelfand, S. Stoffel, S. J. Scharf, R. Higuchi, G. T. Horn, K. B. Mullis and H. A. Ehrlich. 1988. Primer—directed enzymatic amplification of DNA with a thermostable DNA polymerase. Sci. 239: 487–491. (Jan. 29, 1988).

Shibata, D. K., N. Arnheim and W. J. Martin. 1988. Detection of human papillomavirus in paraffin—embedded tissue using the polymerse chain reaction. J. Exp. Med. 167:225–230. (Jan. 1988).

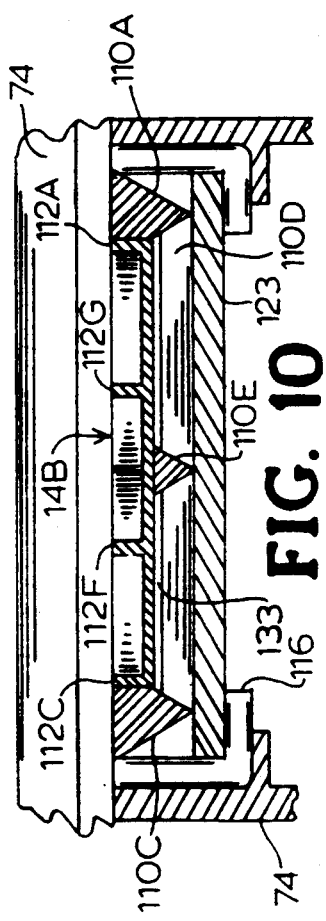
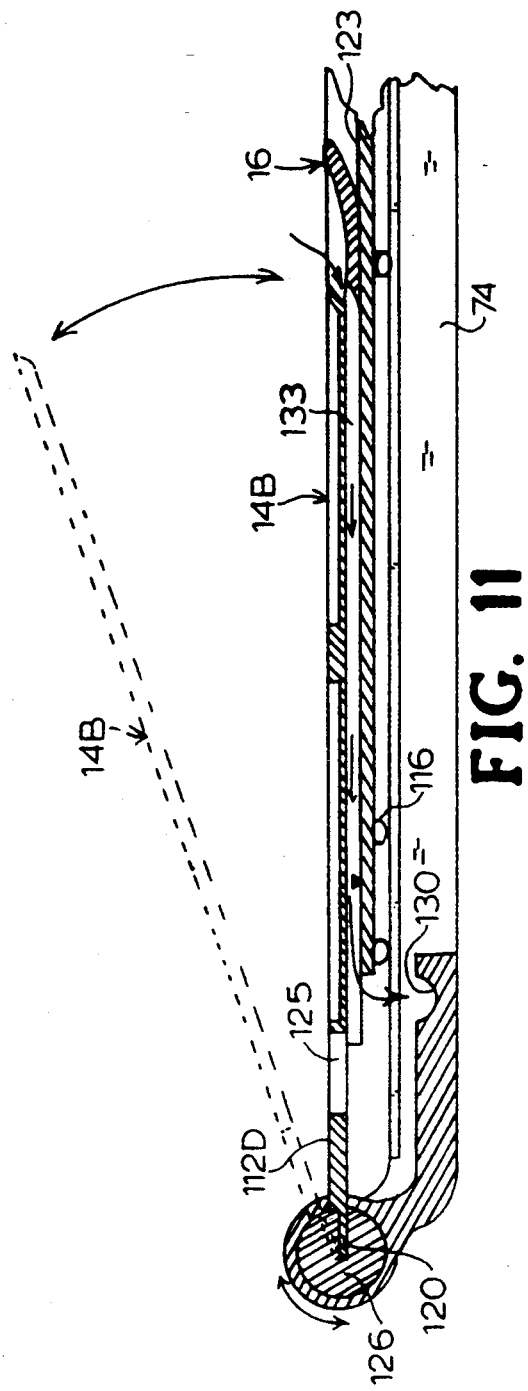

DEVICE FOR PROCESSING BIOLOGICAL SPECIMENS FOR ANALYSIS OF NUCLEIC ACIDS

This application is the national filing of PCT application No. PCT/US90/06768 filed Nov. 16,1990, claiming priority of U.S. patent application Ser. No. 07/438,592 filed Nov. 17, 1989, now U.S. Pat. No. 5,188,963.

BACKGROUND OF THE INVENTION

1. Field of the Invention

This invention relates to a method and apparatus, including component devices, for use in automating the detection of target nucleic acid sequences in biological-containing samples. The method involves a sequence of physical and chemical reactions, and more particularly to a system for the exposure of, amplification of, and labelled-probe coupling to, a specific, known nucleic acid sequence. The process of the invention consists of the following stages: 1) matrix dispensing, sample mixing and DNA immobilization; 2) preparing DNA; 3) amplifying DNA target sequences; 4) hybridizing a labeled probe to the target; and 5) scanning the matrices for signal produced by bound label.

The invention is especially suited to the automated detection of single, specific genetic sequences present at random in multiple samples containing biological material without labor-intensive DNA extraction and purification procedures being performed separately on each sample. The ability to detect single copies of a specific nucleic acid in biological or environmental samples makes this process revolutionary.

2. Description of the Related Art

There is no laboratory apparatus or equipment currently on the market that automates DNA preparation, modification and detection in one, unattended operation. The apparatus and devices described herein embody an automated process, including a fluid-delivery system and a thermal reaction chamber.

Devices for receiving biological specimens for diagnostic purposes are varied and adapted to the methods of detection. The devices may take the form of tubes for liquid specimens, flat surfaces such as glass slides suitable for microscopy, microtiter dishes, Petri dishes and cubes containing growth medium, or filters made of various materials to which cell and viral components will adhere.

These specimen samples are then treated in such a way as to indicate either the presence or absence, or quantity, of a specific biological entity. Test reagents may either be preapplied to the device or added in series after the specimen is present. Test results are read manually by a technical person or automatically with instrumentation specifically designed for that assay. In some instances the specimen is diluted with a diluent, or an aliquot of the specimen is removed from the original collecting device and transferred to another vessel at some point in the assay. In some cases physical and chemical means are used to amplify the signal of the assay for greater sensitivity. Some assays require extraction or separation to isolate a specific component from other parts.

In DNA-based diagnostics the sequence specificity of base-pairing or enzymatic or other types of cleavage is exploited. The linear sequence of nucleotides in double-stranded DNA molecules forms the basis of replication of the genetic code. Hybridization is the binding of two single-stranded DNA strands whose base-pairing sequences are complementary. Temperature and salt concentration affect the stringency of these base-pairing matches. A change from high stringency to low stringency can cause the same DNA probe to be either exquisitely specific to detect a particular target or less specific and detect a group of related targets.

In some instances the sizes of DNA fragments, produced by restriction endonuclease digestion or by amplification of a target sequences between primer pairs, are used to make a DNA-print for individual identification or aid in diagnosis of a genetic disease, cancer or infectious disease. For example, electrophoresis may be used to size-fractionate different-sized nucleic acids which have been specifically cleaved or whose native length puts them in a distinguishable size-length class.

In the electrophoresis method, a current is applied to DNA loaded at the cathodal end of a gel matrix, which causes the DNA to migrate towards the anodal end of the matrix. The electrophoretic mobility of DNA is dependent on fragment size and is fairly independent of base composition or sequence. Resolution of one size class from another is better than 0.5% of fragment size (Sealy P. G. and E. M. Southern. 1982. Gel electrophoresis of DNA, p. 39–76. In D. Rickwood and B. D. Hames (EDS.), Gel Electrophoresis of Nucleic Acids. IRL Press, London). This reference and all other publications or patents cited herein are hereby incorporated by reference.

Electrophoresis methods thus require a vessel to hold the matrix material and the biological specimens to be subjected to electrophoresis. Such vessels may mold the gel matrix during its formation and may hold it during processing.

Diffusion of reagents is faster where the ratio of the matrix surface area to matrix volume is greatest as in thin, flat matrices. Likewise, electrophoresis of macromolecules requires less voltage and is faster in ultra-thin matrices or tiny (glass) capillaries. In these aqueous matrices, the vessel is necessary to prevent evaporation and to add strength in handling. Existing vessels that enclose matrices impede rapid diffusion of reagents and molecular probes. Once the existing vessels are taken apart in processing, they cannot be put back together to continue automated processing.

Accordingly, the invention aims to provide a system for automated gene identification of multiple samples, which prepares nucleic acids in the samples for testing, sufficiently amplifies target nucleic acid sequences and accurately detects their presence or absence in the samples.

Another object of the invention is to provide a carrier to contain specimens and be used as the sole vessel for completion of all steps of an assay, including sample preparation, electrophoresis, amplification and hybridization.

Yet another object of the invention is to provide support of the matrix and specimen, molding the matrix and embedding the specimen in it for automated processing.

A further object of the invention is to provide such a system which is adaptable to dispensing different quantities of different reagents for saturating specimens quickly with a series of solutions automatically.

A further object of the invention is to provide such a system wherein airflow and heating regulate and monitor temperature and humidity in the matrices including drying them.

A further object of the invention is to provide a system which can accommodate partial capacity loads, i. e., fewer matrices per run, or that can accommodate more than one probe per run.

A further object of the invention is to provide an automatic process and apparatus allowing identification of nucleic acid sequences that have been embedded or fractionated in a matrix whether or not prior extraction or purification of DNA has been performed in the invention.

A further object of the invention is to carry the specimen in transport from the point of collection to the processing point.

A further object of the invention is to provide a convenient way to make the particles containing target nucleic acids of a specimen in a matrix available and sufficiently spread for signal detection in a two-dimensional array.

A further object of the invention is to concentrate specimen nucleic acids, or amplified products thereof, for detection of their presence.

A further object of the invention is provide a barrier to evaporation of solutions during processing.

A further object of the invention is a mechanism to change configuration of the carriers during processing of the specimen to adapt to processing conditions.

A further objective of the invention is to provide support for reading the test results.

A still further object of the invention is to permanently store the nucleic acids present in the specimen for possible retesting and serve as a permanent record of the test, if an archival record is desired.

Other objects and advantages of the invention will be more fully apparent from the ensuing disclosure and appended claims.

SUMMARY OF THE INVENTION

The process and invention in this patent utilizes the fundamental methodology from several state-of-the-art techniques to automate nucleic acid detection directly from biological material. The direct detection is automated by immobilizing the nucleic acids of each sample in a semi-solid matrix for DNA preparation, amplification and hybridization. The frequency of the target sequence in the sample can be determined by measuring hybridization of the label to the single gene targets in situ.

In addition, the apparatus of the invention may be used to process gels of other known techniques in a new way and to automate these techniques or increase their sensitivity.

In a broad aspect, the component device of the invention comprises:
  a top piece and a bottom piece, said bottom piece having a matrix holding area, said top piece having a closed position;
  said top piece and said bottom piece hinged together along a first side of said bottom piece, said top piece having a first area that extends beyond said first side, whereby force on either piece causes the top piece to hingedly move away from the bottom piece and upward from the closed position to an open position; and
  said bottom piece having an overlap area on a second side of said bottom piece, said overlap area extending beyond said top piece, said overlap area having a fluid receiving depression, whereby fluid added to said fluid receiving depression may diffuse into and over matrix material placed in said matrix holding area.

The bottom piece and top piece are preferably parallel to each other except where the matrix is not of a uniform thickness.

In more detailed aspects of the device of the invention, the "first side" of the bottom piece may be an end or a long side of the preferably elongated bottom piece. Thus, in a first embodiment of the carrier device of the invention the top piece is hinged to the bottom piece along a short edge of said bottom piece and towards the short edge of the top piece, and said first side is opposite and parallel to said second side.

In a second embodiment of the device invention, the top piece is hinged to the bottom piece along a side edge of said bottom piece and said top piece, and said first side is perpendicular to said second side.

In the device of the invention, multiple carriers are housed in a reaction chamber through which reagents, solutions, enzymes and nucleotide primers and probes required for identification in this system are circulated. The carriers are stacked, preferably in a horizontal plane, and remain relatively stationary. Fluids move through the matrices and the spaces between them and the carrier covers. The liquid buffers and washes are delivered into the reaction chamber, and gravity flow through the thin matrices and dehydration/rehydration of the matrices facilitate and control diffusion. This approach contrasts to the way that dried agarose gels or solid-support systems such as filters are agitated in hybridization solutions.

The method of the invention utilizes the component device of the invention. The DNA present in the sample, that has been introduced into an individual matrix in a carrier, remains anchored in the corresponding matrix and is separated from the other cellular particles or sample debris by lysing solutions and thorough washing. Several volumes of wash buffer are diffused through the matrix to clear away biological molecules (except nucleic acids, which are immobilized because of the nature of their structure) and also matrix contaminants (for example, sulfonated groups found in agarose) that might interfere with subsequent enzymatic activity. The wash solution also normalizes pH. The matrices are dehydrated by a drying cycle. The sample to be analyzed for the presence of a particular DNA component (or RNA or polypeptide moiety) is thus suspended in matrix material placed in the matrix holding area of the device.

Any one or more of the following steps may then be performed on the matrix and suspended sample, depending on the sample and the results desired: (a) removal of undesired components, e.g. cell wall material, proteins, etc., (b) denaturing the DNA in situ, (c) amplifying a desired nucleic acid component in the matrix material; (d) applying an electric current to the matrix material; and (e) hybridizing a labeled probe to a desired component. Subsequent steps known in the art may be used to detect the particular component in the matrix, or the component as amplified and/or labeled in the matrix.

The device of this invention facilitates automation of DNA-based diagnostics and genetic surveillance and detection. Although the discussion and examples herein are directed primarily to DNA analysis, it is clear that the device of the invention may be used with RNA with equal facility. The device of the invention serves as the specimen container. It can also serve as a mold for embedding a specimen in its matrix. It serves as a specimen holder for manual and mechanical handling and transport. The device serves as an individual archival record for each sample specimen. The sample nucleic acids are preserved in such a way that they may be tested more than once, or the sample may be analyzed for the presence of other nucleic acid targets.

Its parts are configured to open and close via a hinge connection. The closing mechanism (not shown), which is incorporated into the automated instrument, may open and close the hinged parts. The invention may also be opened and closed manually.

One way the invention is different from other diagnostics is that in the invention nucleic acids in specimens may be dispersed randomly in the matrix, and detected as individual targets in the specimen. The significance of this two-dimensional format is that target nucleic acids in spread or dispersed cells or viral particles are enumerated in order to quantify the number of cells or viral particles containing the suspected target DNA. A given degree of amplification of target DNA in a matrix will distinguish locations that represent a few copies of original target from many copies of target. The difference in amplitude of these signals, and construction of a total signal by summing individual signals, reflects a more accurate quantitative answer for each specimen as opposed to measuring a single amplitude for total signal of each specimen. In addition to improving measurement of signals over background noise, the method is useful to distinguish individual particles/cells having a few copies of a target DNA from those with many copies. This information can be predictive (1) in cancer when in vivo gene amplification means a more aggressive malignancy or (2) in viral infections to distinguish latent from active infection.

DNA sequences are excellent molecular probes because of the complementarity of primer and probe sequences to target DNA for the purpose of amplification and hybridization. Similarly the recognition sites of restriction endonucleases are DNA-sequence specific. Restriction fragment length polymorphisms (RFLP's) are the result of restriction endonuclease cleavage and require electrophoretic size fractionation. Detecting a particular sequence variation may indicate individual identity, disease susceptibility or disease state.

To perform amplification and/or hybridization, the gel matrices are dehydrated by the introduction of heated, moving air while the gel matrices remain stationary in the reaction chamber. The matrices are then rehydrated with the solution containing primer, nucleotide and polymerase molecules. The DNA is amplified by rounds of primer extension of target DNA. A short time is allowed for annealing of one or more primer pairs (a pair is defined as two primers that border opposite ends of a linear target DNA and are complementary to the opposite DNA strands) at an appropriate temperature. The number and choice of primer pairs and the number of replication cycles will vary according to the target nucleic acid. The sequence of a target nucleic acid must be known to determine a system to be used for detection. As more sequence information becomes available, the choice of primers for any one system may be changed to reflect a conserved genetic region and improve the specificity of detection. New technology may improve fidelity of primer annealing and DNA polymerization to allow accurate detection by incorporating labeled nucleotides in the amplification step, thus eliminating the need for a separate hybridization step in the detection process.

The gel matrices are dehydrated after the gene amplification reaches the level needed for detection by the hybridizing probe. The hybridizing probe consists of single-stranded DNA complementary to, but shorter than, the DNA target sequence and has one or more label molecules attached. The choice of nucleotide sequences for the hybridization probe reflects the same considerations stated for primer sequences. The hybridizing solutions are pulse-sprayed into the reaction chamber. Shorter DNA probes diffuse and bind to the amplified copies within the matrices, while diffusion conditions retard leaching-out of the longer, amplified segments or the carrier surface may be used to trap small amplification products.

An alternate procedure involves primer pairs back to back along a target sequence in order to extend longer targets efficiently. The number of primer pairs in a linear or nested series may vary to accommodate the size-length of DNA required to immobilize the amplified segments during treatment. This alternative requires a ligase to incorporate each primer covalently to the linear molecule at its 5-prime end and the ligase needs to be thermo-resistant. In a particular system, such an enzyme would need to be isolated from nature, if it has not been already isolated.

Another alternate procedure involves adding the hybridization probes during the amplification phase. When single-stranded, labeled probe molecules are incorporated into the growing chains, they become part of the amplified DNA and sequential hybridization is not necessary. Since the process time is dramatically reduced in simultaneously amplifying and labeling the DNA, this step is desired. An enzyme for joining single strand nicks as described in the preceding paragraph is also necessary in order to insure the target sequence was labeled unambiguously over a background of randomly-primed, amplified DNA.

Each kind of labeled probe that hybridizes to the target DNA is detected according to the nature of its label molecule. The number of aggregates of detection signals corresponds to the number of original target sequences directly. In the case of higher density of targets or remelted agarose, the number can be interpolated.

Either specific restriction endonucleases, ribozymes (non-protein RNA molecules that cut and resplice RNA into genetic messages) or polymerases may be introduced into the gel matrix to act upon the nucleic acids, which are selectively embedded. "Selectively embedded" means that the nucleic acids of specimens are trapped and other specimen components and excess or unbound reagent molecules are washed away. Experiments have shown DNA sequences of a few hundred nucleotides or more remain essentially immobilized during amplification and hybridization conditions in given matrix materials while allowing short oligonucleotides, mononucleotides or enzymes to diffuse as necessary. The composition and concentration of the matrix may be altered to selectively immobilize a specific size class of nucleic acids. The endonucleases break linear DNA into restriction fragment polymorphisms. Polymerase molecules, together with DNA or RNA primers, are used to expand a selected DNA or RNA fragment population. With addition of electrical current, the fragments move through the gel matrix toward the anode, according to their size. Subsequent staining or hybridization within the matrix and carrier enables the identification of specific band patterns. Amplification products may be identified by electrophoretic separation and non-specific DNA staining; but in some cases hybridization probes are necessary to distinguish them from spurious amplification products which cause ambiguities.

The purpose of the electrical current in electrophoresis within the device of the invention is to fractionate and concentrate the macromolecules by size. Electrophoretic mobility of specific DNA restriction fragments, RNA messages or amplified nucleic segments are then compared with those similarly treated from another specimen. For example, specimens from two or more individuals may be compared for paternity identification. Forensic specimens may be compared to specimens from suspects. Family groupings may be compared for markers of genetic disease. Tumor specimens may be compared to standards for classification.

The electrophoretic character of this device is different from other electrophoresis equipment in that the macromolecules in the matrix are automatically processed before, after or in between electrophoretic phases. Different fluid treatments are applied automatically in series to the matrix carrier. The ability to automatically change the solution saturating the matrix heretofore was not possible. The instrument provides processor-controlled fluid delivery to individual matrices. An equivalent electrical current is supplied to each matrix carrier in each rack by design of the circuits.

Previously, unrelated specimens were grouped together in the same non-standardized gels. In this invention, related specimens contained in each matrix are processed and compared with both a standard built into each matrix and a standard matrix processed with each instrument operation. The carriers and matrices are preferably manufactured according to specifications that will standardize them and make their electrical resistance equivalent, when saturated with buffer, whereby the interpretation of the test results determined from them may be standardized and variability originating from individual gel preparations eliminated.

In standard electrophoresis the prepared sample is manually loaded in the gel for electrophoresis, and the gel, or the nucleic acids in it, are manually handled for hybridization and detection. The feature of the matrix carrier of the invention is that the physical and chemical handling of it is automated within the instrument. Other kinds of prepackaged, prepared gels for electrophoresis are opened before or after electrophoresis and the gel is removed for running, staining or other processing. This carrier is unique in that it can be opened and closed mechanically by the instrument in coordination with the fluid and air flow systems in the thermal chamber of the instrument. This feature allows the genetic specimen to undergo further treatments without transfer to another vessel.

Furthermore, the automated system represents versatility in applications. A unique matrix carrier is intended for each specific diagnostic or DNA identification test. Matrix size and composition will be adapted to perform a particular kind of assay. The two-dimensional format allows spatial enumeration of signal identification positions of target sequences during repetitive probing.

Racks are designed to hold matrices of the same design. The same basic instrument design will hold any rack configuration and accommodate processing for any of the tests. It is also clear that instead of or in addition to using the carrier for electrophoretic separation of DNA or RNA, the carrier may be used for analysis of sample proteins using standard electrophoretic techniques or in situ immunohistochemistry.

Sequence-specific nucleic acid identification depends upon one or more of three fundamental methods: amplification, hybridization and electrophoresis, all of which may be performed using a matrix carrier according to an embodiment of the invention. The automated system for DNA-based diagnostics herein incorporates one or more of these methods in a given order depending upon the nature of the specimen and the quantity of nucleic acid in a particular type of specimen. Microprocessor-controlled processing starts with a sample preparation phase. Lysing and deproteinizing treatments are performed automatically to prepare the sample specimen after it is incorporated into the matrix carrier and loaded into the instrument. The application of treatments that follow are programmed to perform methods appropriate and prearranged for a batch of similar matrix carriers.

As illustrated in the schematic of FIG. 17, the automated system has great flexibility in the inclusion and ordering of methods used. After sample preparation any one of the three fundamental methods are performed first: amplification, hybridization or electrophoresis. Detection of the sequence-specific nucleic acid target may occur after treatments for any one of the methods. A particular test can involve one, two or all three methods before detection, in any order.

Furthermore, there are advantages to performing multiple steps or methods in one vessel. They are: (1) standardization of accurate assay results (2) less technician skill and less technician preparation and handling time required and thus lower test cost (3) more convenient sample collection and (4) less human error in switching samples or labels. Current methods require a technician to prepare a sample and transfer it to another container or a gel together with other specimens. A specimen may go through several container changes during processing, and each container change is a possible source of error in identifying a patient specimen or sample source. The matrix carrier in this invention contains the patient specimen or sample throughout the entire processing. The uniqueness of this technology is the stabilization of nucleic acids in a matrix without extensive preparation of the biological sample, and the subsequent treatment of this matrix to prepare and identify the target genetic sequences automatically.

The invention includes any possible coating of the carrier surfaces with selected biomolecules, natural or synthetically-manufactured, by chemically attaching them to the carrier material. For carriers made of glass, a known standard method of binding biomolecules to surfactants is with sulfonyl chlorides (Nilsson et al., In W. B. Jakoby (Ed.) Methods in Enzymology, Vol. 104, 1984, Academic Press, Inc., Orlando Fla.). For carriers made of polypropylene or polystyrene, chemical attachment may be by hydrophobic binding to their phenyl groups. The purpose of adhering molecules to the carrier is to facilitate the processing of genetic detection.

For a fuller understanding of the nature and objects of the invention reference should be made to the following detailed description taken in connection with the accompanying drawing figures.

BRIEF DESCRIPTION OF THE DRAWINGS

FIG. 10 is a cross-section view of the snap-on base and cover of the third embodiment as it would be placed on a standard slide in the rack.

FIG. 11 is a lengthwise section drawing of the snap-on base and cover of the third embodiment to show liquid flow and cover positions.

DETAILED DESCRIPTION OF THE INVENTION AND PREFERRED EMBODIMENTS THEREOF

Figure 1:
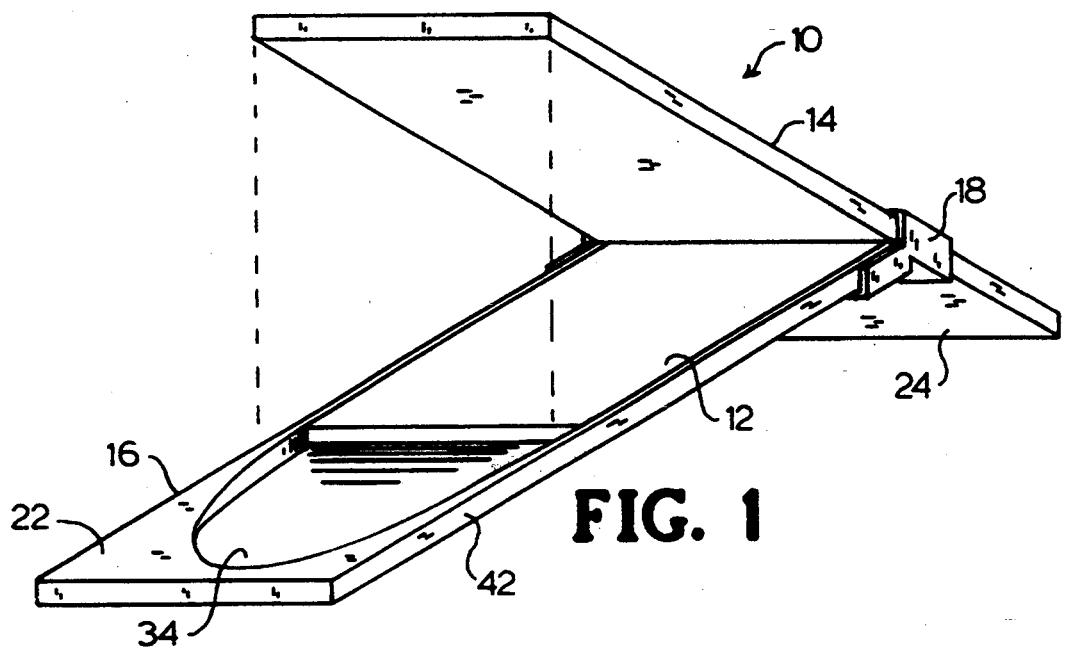
FIG. 1 is a perspective view of a first embodiment of the carrier of the invention in an open position.
Figure 2:
FIG. 2 is a side view of the first embodiment of the carrier of the invention in a closed position.
Figure 3:
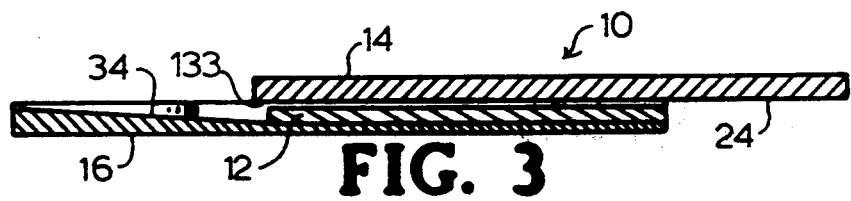
FIG. 3 is a side view of the first embodiment of the carrier of the invention with carrier edge removed showing the matrix space and the channel.
Figure 4:
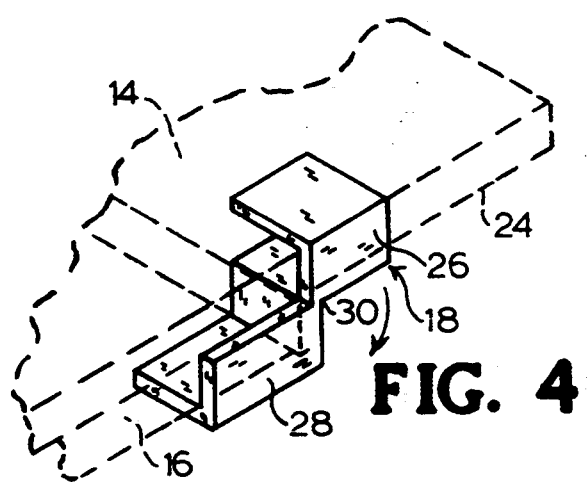
FIG. 4 is a perspective view of a hinge of the first embodiment.

The invention broadly comprises a fluid flow system comprising an apparatus and component carriers 10, each of which carrier contains biological specimens in a matrix 12. The system, shown in FIGS. 1–14 & 16, is capable of fluid flow through the matrices and collection of fluids drained from the reactor before being either discarded or recycled. The system also includes blowers and heating elements to control the air or fluid temperature in the chamber. In the preferred embodiment of the invention, the programing of the number and time intervals of treatments, the endpoints of each treatment, valve-control and electrical switching are computerized into the microprocessor.

The carrier 10 is composed of an upper rectangular piece 14 and a lower rectangular piece 16 hinged together; which, when folded, encase the matrix 12 and, when unfolded, expose one surface of the matrix 12.

Three embodiments of the carrier device are depicted in the figures. The first two embodiments may have electrical contacts for electrophoresis and all may have multiple matrix sections and subsections, but for ease of depiction, these variations are not shown in all embodiments.

In a first embodiment (FIGS. 1–4) the hinges 18 are along a shorter side of the lower rectangular piece 16, while in the second embodiment (FIGS. 5–7), the hinges 18 are along a portion of a longer edge of the lower rectangular piece 16. Having the longer side portion of the lower piece 16 be hinged (second embodiment) is valuable for electrophoresis, where a longer matrix is preferred. Such a side hinge arrangement allows a longer, narrower matrix while requiring less overhead space for opening the carrier than an elongated cover for a carrier that was hinged at an end would require.

The edges of the two pieces 14 and 16 are juxtapositioned to overlap each other so that in the first embodiment (FIG. 1) the upper piece 14 overlaps and extends beyond the lower piece 16 at the end having the hinge 18, and the lower piece 16 extends beyond the upper piece 14 at the end of the carrier 10 that is not hinged. In the second embodiment (FIG. 5), the upper piece 14 extends beyond the lower piece 16 at the hinged side of the lower piece 16, and the lower piece 14 extends beyond the upper piece 14 at an edge perpendicular to the edge having the hinge 18.

The overlap 22 on the lower piece 16 functions to receive fluids which may diffuse into the matrix 12 whether the invention is in the closed or open position. The upper overlap 24 of the upper piece 14 may function as a lever end to open the invention. The upper piece overhang is not essential for opening or closing; it helps fluids exit the diffusion zone by allowing droplets to collect and drip when their weight overcomes the surface tension of the droplet. After a drip, the area starts collecting again to repeat the flow out.

Each hinge 18 (FIG. 1) in the first embodiment preferably comprises an upper portion 26 grippingly engaging the upper piece 14 of the carrier and a lower portion 28 attached to the lower piece 16. The means of attachment may be glue or other known means of attachment. A flexible bend area 30 located between the upper portion 26 and the lower portion 28 enables the hinge movement and the opening and closing of the carrier 10. The hinge 18 may be made of flexible plastic, or may be made of a rigid material such as a plastic or metallic alloy, except in the flexible bend area 30. Preferably such a hinge is attached at each side of the carrier 10. Although the carrier is described as comprising separate pieces, it is equally possible that the carrier may be molded as one piece with a "living" plastic hinge connecting the portions or that two or more components of the carrier may be molded together.

The system also includes a pump to maintain pressure in the jet-spray manifold during fluid flow. A system of valves controls selection of the treatments that will diffuse though the matrices and circulate through the system. The valves operate in the connections between the reactor chamber and the reservoirs which hold the reagents. A water line connects to the system through a valve and a regulator limits the maximum pressure. The pump is activated for auxiliary pressure if the water pressure reaches a designated lower limit.

Treatment solutions from fluid lines 32 flow or drip into fluid-receiving area(s) 34 on the lower piece 16 and diffuse into the matrix 12. The fluid system delivers measured volumes from one of multiple reservoirs through a common line either in a continuous or pulse mode at a selected flow rate. Fluid application is also important in opening and closing the carrier halves 14 and 16. Application of a fluid volume at the time of opening releases surface tension between the upper piece 14 and the matrix 12. This action reduces the mechanical force required to separate the upper piece 14 from the matrix without disturbing the matrix 12. Application of fluid to the upper surface of the matrix 12 prior to closing the carrier pieces 14 and 16 leaves a liquid film between carrier piece 14 and the matrix 12 upon closing. Closure of the carrier 10 at the hinged joint 18 brings the surface areas that are closest to the hinge 18 together first and gradually those farther away from the hinge 18 make contact. The wave-like closing action smoothes out bubbles whose presence may cause aberrant test results.

The fluids from channel 34 saturate the matrix 12 and fill the space between matrix 12 and the upper half of the carrier 14, and create a layer of washing solution 133 in immediate contact with the matrix. This liquid layer acts as a diffusion zone for molecules from the solutions being added to the carrier to diffuse into the matrix or molecules within the matrix to diffuse into the solutions leaving the carrier, whereby solution flow, rate, volume, temperature, and molecular size, charge and concentration in the diffusion zone affect diffusion within the matrix.

The matrix allows entry and exit of reagents by diffusion to expose nucleic acids for identification by nucleic acid hybridization and/or antibody binding. A diffusion pressure is exerted on the gel matrix that maximizes molecular reaction kinetics. The matrix material allows diffusion yet maintains its integrity throughout the treatments that require nucleic acid immobilization. In the first stage of the invention, the dry matrix material is mixed with an aqueous buffer and kept liquid while sample is added, dispersed randomly throughout and poured into a mold. The preferred matrix material is agarose, a hydroid colloid, because the procedures for amplifying and hybridizing DNA have been accomplished in agarose. The matrix is solidified by cooling it to a lower temperature or by chemical means to immobilize the sample in the matrix. Drying steps during and between some treatments dehydrate the matrix blocks and the subsequent hydration with other liquid treatments enhances diffusion by creating a sponge-like uptake.

Figure 12:
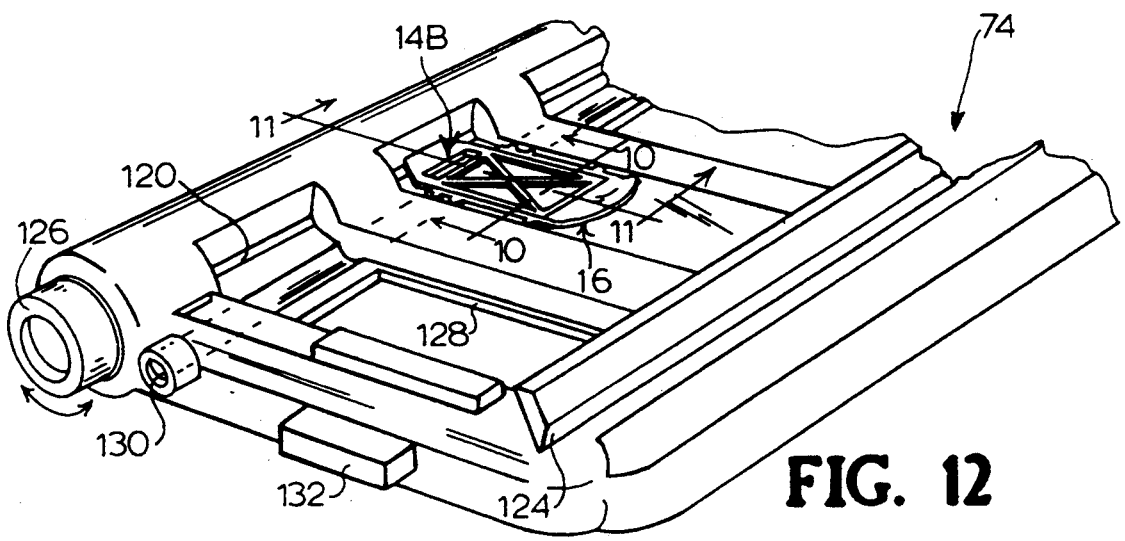
FIG. 12 is a perspective view of a tray rack to hold the matrix and carriers.

Excess and waste liquids may exit at the opening(s) 36 between the hinged pieces 18. Collecting troughs 130 on the racks 74 within the instrument provide for fluid disposal (FIG. 12). Any opening(s) along the edge are plugged during addition of the matrix material to the carrier 10 when the carrier is being prepared for use until after the matrix 12 has been formed. Taping the opening(s) may be used to close them, but other means of temporarily covering the opening are possible. The tape or other fastener is removed when the carriers 10 are loaded in a rack, or a sealed barrier over the opening(s) may be broken by the opening or closing action of the carrier pieces 14 and 16.

Opening 36 between the hinges 18 or an open side or end of the matrix 12 also allow electrical contact with the matrix material. The electrical contacts 38 and 40, in each embodiment and shown for the second embodiment in FIGS. 5 and 6, permit a constant or deliberately variable electrical current to flow through individual matrices in order to optimally resolve different size classes of macromolecules. A coating with negatively charged groups such as Nafion TM (DuPont Co., Wilmington, Del.) on the lower surface of the upper carrier half 14 and/or the upper surface of the lower carrier half facing the matrix 12 may be used to help reduce electroendosmosis, in which cations in aqueous fluids and hydrogels tend to flow toward the cathode.

The carrier pieces 14 and 16 may be made of glass or plastic or combinations thereof, sheets of polymer (for example, polyetherimide, Ultem TM, General Electric, Pittsfield, Mass., or polycarbonate, DuPont Co., Wilmington, Del.) or metallic alloys. Carriers used for assays involving electrophoresis are made of non-conducting materials in order that current flows through the matrix and not the carrier. Parts of the carrier may be made of optically clear material for scanning the matrix.

The matrix 12 is preferably a semi-solid material made with agarose or acrylamide or similar polymer, or mixture thereof, that incorporates several times its weight of an aqueous solution (hydrogel). A liquid specimen or specimen mixed with a liquid diluent may be added to the carrier at channel 34, or into subsections 46 directly, from where it either combines with a liquid matrix 12 or diffuses into a pre-formed dehydrated matrix or a subsection thereof. Application of heat or a polymerizing agent incorporates the specimen into the matrix 12 or subsection thereof, forming a gel matrix with embedded specimen. The gel matrix or a subsection of the matrix may be hydrated or not before loading its carrier in the instrument. If dehydrated in storage or transport, the gel matrix material is rehydrated with fluid treatments from the fluid lines 32 of the instrument. A rehydrated matrix, preferably ultra-thin (less than 500 micrometers thick), facilitates diffusion of small molecules and retention of larger ones, quicker electrophoretic resolution and better detection of signal.

A subsection of the matrix (either dried matrix material itself or a strip of other absorbent material along the edge of dry matrix material or the area where matrix will be formed) may act as a wick to spread a liquid specimen by capillary action across one dimension of the matrix, specifically from the point of addition at one end of the absorbent material to its opposite end. The purpose of this subsection is to dilute biological particles in the specimen sample as they trail the solution's leading edge. The release of liquid matrix material evenly across this first dilution (at 90 degrees to it) has the effect of diluting the particles in a second direction. Diluting the biological particles in this way creates a two-dimensional dilution gradient which is significant because individual genetic targets or the density thereof may be detected and yield quantitative or semi-quantitative measurement of the frequency of the biological particle. If known amounts of biological specimens are diluted in this way, it is possibly to identify individual biological particles of specific genetic character by molecular means if sufficiently spread in the matrix, even after using means to multiply the number of genetic targets within each biological particle. Multiplied copies of genetic targets spread slightly from the site of the original copy and increase the ability of a digitized pattern of image analysis to detect labeled molecules incorporated into the cluster. The ability to distinguish clusters from random, non-specific labeling is advantageous in quantifying the biological particles by enumerating clusters of specific genetic targets. The ability to make the dilution gradient automatically as the specimen enters the carrier eliminates the need to make a dilution series and eliminates having to process each dilution of the sample in a separate matrix.

The carrier 10 may be molded to have edges 42 or the carrier halves 14 and 16 may have edge pieces fastened to them. The edges 42 are formed in order to enable molding of the matrix material in a space between the upper and lower carrier surfaces 14 and 16. The space between carrier surfaces 14 and 16 may diverge from one end to the other by placing wedge-shaped edges 42 along the sides in order to form the matrix material thicker at one end (not shown). Such a wedge-shaped matrix may be made by pouring molten matrix material into a wedge-shaped enclosure formed between the upper and lower carrier surfaces and bounded by edges 42. One purpose of a wedge configuration is for increasing the electrophoretic separation of a wider range of nucleic acid fragment-size classes over less linear space.

Another aid to better resolution of fragment populations is variation of the concentration of the matrix material over the linear path of electrophoresis, i.e., making a gradient gel matrix. When matrix material is preformed on carrier half 14 or 16, it may be applied in a manner to form a concentration gradient or wedge across one dimension for better electrophoretic resolution.

Figure 5:
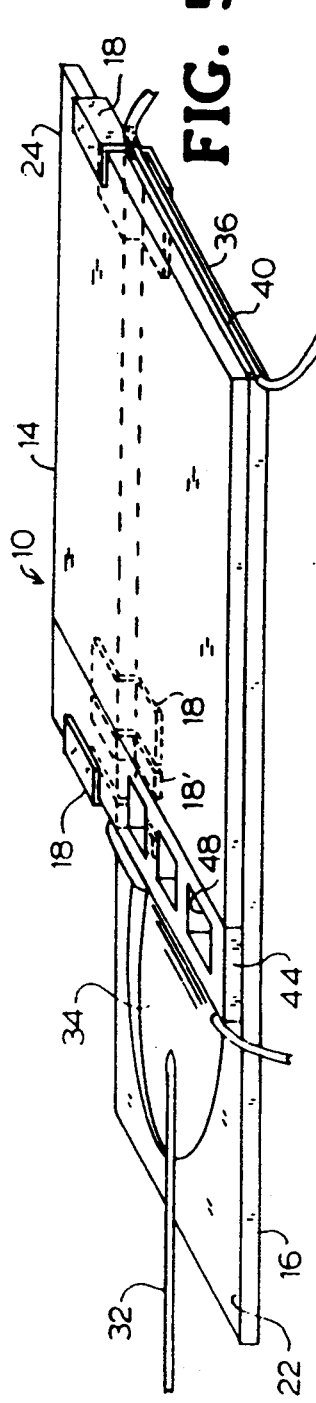
FIG. 5 is a perspective view of a second embodiment of the carrier in a closed position.
Figure 6:
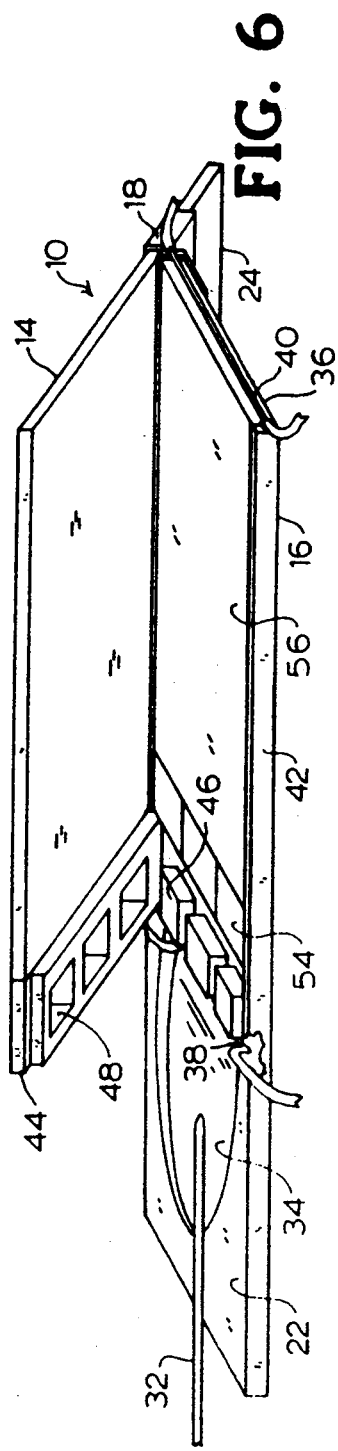
FIG. 6 is a perspective view of the second embodiment of the carrier of the invention in an open position showing a side hinge and subsections of a matrix.
Figure 17:
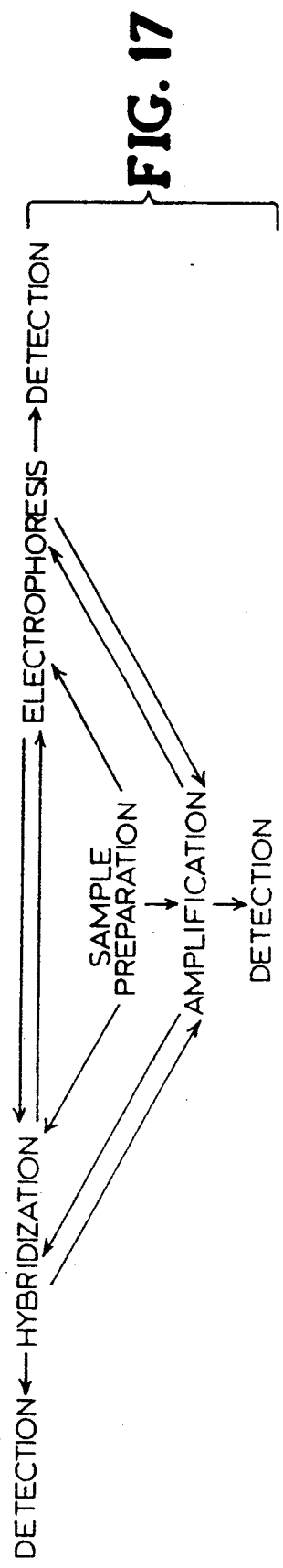
FIG. 17 is a schematic diagram showing some of the various analyses and methods for which the invention may be used.

Edges 42, and extensions 44 which may overlap the surface of the lower carrier section 16, are molded or fastened to one or both of the carrier halves. Edges 42 and extensions 44 may form molds for matrix materials, with and without added specimen material. They may be designed to mold either matrices 12 of uniform thickness in the space between the upper 14 and lower carrier 16 surfaces or mold subdivisions of the matrices 12 that contain different matrix materials and reagents, volumes or concentrations thereof (FIGS. 5 and 6). Similarly the specimen concentration may be diluted between opposite edges of the matrix or from subsection to subsection to improve detection of signals in less concentrated areas. The edge 42 in FIG. 6 is shown cut away where electrical contact 38 crosses it. The extensions 44 may form molds 48 on the lower carrier section 16 and subdivide the matrix area into smaller subdivisions. The subdivision of matrices on one carrier allows the different matrix sections to include different specimens or standards and/or to include reagents or media previously prepared and packaged with the carrier.

Another version of the carrier is for the purpose of making possible antibody or DNA-based testing of fresh, frozen or paraffin-embedded sections in the instrument system so that it is convenient to view the section under the microscope. The advantage to this version of the carrier 10, as shown in FIGS. 8–11, is that its cover 14B and base 16 are snapped onto existing slides prepared with tissue sections, processed in the racks in the instrument, and then carrier parts removed for easy viewing on the microscope stage. This version uses the same fluid flow dynamics as previously described in this patent. The frame pieces of the base 110A–E come in contact with the tissue section and are tapered towards the tissue sections so as to seal fluids from leaking under them. Frame pieces 110D and 110E are lower than frame pieces 110A, 110B and 110C in order to frame the matrix but allow the cover to adjust downward to rest on the matrix after it dries. Frame piece 110B includes fluid receiving area 34. The fluid-receiving area 34 includes a step 122, sloping up to the same height as frame pieces 110D and 110E.

The cover 14B in this embodiment is constructed very thin in order to reduce thermal mass and make it more responsive to temperature changes. Frame pieces 112A–D and the raised criss-crossing struts 112F–G on the upper surface may be thicker to increase strength for lifting the cover. The frame piece 112B tapers and flares gradually away from the fluid-receiving area 34 below so fluids are more easily drawn into the matrix-holding area 12. The frame piece 112D includes an opening 125 so fluids leaving the slide form droplets and a tab 118 that fits into the slot 120 of the cover actuator 126 in the rack 74.

Thin histological sections are placed on standard microscope slides. A carrier base 16 is snapped over the specimen section of a slide 123 by applying pressure under the slide and over the frame pieces 110A and 110C to spread apart the snaps 116 and fit the slide into the base. The individual sections cut from a tissue block may be considered a matrix 12 for the purposes of treating the specimen in the carrier device and accompanying instrument, or additional matrix material may be added over the tissue section to form a matrix 12. The cover actuator 126 raises and lowers the cover 14B so it rests on the tissue section/matrix 12 adjusting to the height of the tissue section/matrix 12 before and after drying or to the frame pieces 110D, 110E and step 122, if the dried and rehydrated matrix surface is lower than the frame pieces. The fluid-receiving area 34 funnels applied fluids to the matrix/tissue section 12 and fluids fill the washing zone 133 between the top surface of the matrix/tissue section 12 and bottom surface of the cover 14B. Frame piece 110B flares out and up to hold fluids in the fluid-receiving area 34. Two subsections 46 of the matrix 12 are illustrated to show that two or more different kinds of DNA probes or antibodies may be applied and processed in parallel on the same tissue specimen/matrix. Two or more bases may be connected as one unit that allows two or more slides to be snapped into place in the unit and thus loaded together into the instrument for processing.

With any of the embodiments of the carrier, introducing the specimen into the matrix allows pretreating the specimen within it to prepare DNA in the sample by a standard method of Smith, Klco and Cantor (1989, In K. Davies (Ed.), Genome Analysis-A Practical Approach, 1989, pages 41–72, IRL Press, Oxford) or by variations of a standard method. In a multisection matrix, another section of the matrix may be pre-formed on the carrier and accept DNA molecules transferred to it from the initial matrix via electrophoresis. The purpose of varying materials, or the volume and concentration thereof, in submatrix sections on the same carrier is to optimize conditions for a specific method. For example, polyacrylamide gel reagents may be introduced, dried and enclosed in one section of the carrier during manufacture. Later, the sample is mixed with liquid agarose and added to the matrix carrier 10 filling subsection spaces 48 and forming subsection 46. After sample preparation treatments and subsequent drying of the agarose matrix in subsections 48, the carrier 10 is opened and electrophoresis buffer applied to all matrix sections. The nucleic acids (or proteins) are electrophoretically transferred from the agarose to the acrylamide matrix (or an intermediate matrix in subsections 54) for a processing step for which acrylamide is better suited than agarose.

The first matrix the specimen encounters may serve to cleanse it. Drying and rehydrating this matrix reduces total volume and thus concentrates samples. Electrophoretic movement of macromolecules from the concentrated first matrix into the second matrix has the effect of loading a more concentrated sample onto the second gel, i.e., more sample target molecules per unit matrix. The more concentrated the macromolecules are when starting electrophoresis, the more easily detected they are after electrophoretic separation due to a narrower band width. The process of this invention overcomes the difficulty of loading enough sample per unit volume on the thin gels. Our research has found that samples migrate from a dried gel into a second matrix.

Research shows further that an added advantage of using a dried matrix is that macromolecules migrate slower in a dried and rehydrated matrix because the pore size is changed by effectively increasing the matrix substance concentration in the hydrogel. We have also observed the percentage shrinkage of a dried and rehydrated flat hydrogel is several times greater in its thickness than in its length or width.

Thus, the advantages of a dried and rehydrated hydrogel are that: (1) it may be more easily manufactured with a lower concentration of matrix material because later drying will increase the concentration; (2) it may be stored dry; (3) the thinner gel may be rehydrated with less reagent volume than a thicker gel; and (4) the thinner gel that results from the drying and rehydration allows better signal detection than a thicker gel. While other hydrogels may be dried before use, this invention permits automatic changes between alternate drying and saturating processes by opening and closing the carrier without removing either the matrix from the carrier or the carrier from the rack.

The extensions 44 may be raised after the matrix sections are molded. The same mechanism (manual or mechanical, as discussed above) that opens the carrier halves 14 and 16 may serve to remove the extension sections 44 from the matrix 10. When the carrier halves 14 and 16 are opened at the hinge joint 18, the extension 44, which was separating two or more submatrices on the carrier, is no longer positioned between the submatrices. Gel-to-gel or gel-liquid-gel contact allows the parallel transfer of nucleic acids from one submatrix to another by electrophoresis. In the second embodiment, the extension 44 may be opened separately from the opening of carrier halves 14 and 16. Thus, gel matrices on the same carrier may receive isolated treatment or be treated together with any other.

The purpose of two or more matrix sections is to separate functions or samples within one carrier. It is useful then two or more patient specimens are compared in the same carrier or when one matrix section serves one function and the second matrix section serves another function. Examples of different functions are: (1) cleansing nucleic acids in a specimen from interfering biological material; (2) amplifying the nucleic acid fragments; (3) hybridizing a labeled probe to the nucleic acids; (4) fractionating nucleic acids according to size by electrophoresis; (5) comparing an internal standard on the matrix with an unknown; and (6) comparing band patterns to indicate related individuals.

In the system of the invention, the racks 74, as shown in FIG. 12, are designed to fit into the instrument's thermal chamber. The rack 74 services the carriers 10 with one or more utilities from among the following: a hinged or snap-type retainer 124 to hold carriers in the rack, actuators 126 to open and close the carrier cover 14 or tilt the carrier, frames 128 which position carriers for heating and fluid delivery, electrical connections 132 and/or coils for heating the matrix and/or electrophoretic separation in the matrix and a collecting trough 130 which allows drips of waste fluids leaving the carriers to collect and be carried away. The actuators function as hinges for the snap-on embodiment of the carrier (FIGS. 8-11). The racks are designed in such a way that they position each of the matrices 12 at the opening of a fluid line 32 for fluid delivery from fluid reservoirs. The racks may support the carriers 10 in any designated plane, horizontal, vertical, or diagonal. Tilting the carrier may serve the purpose of increasing the rate of fluid flow when necessary. Another version (not shown) of the racks would have actuators positioned to allow the cover to open for FIGS. 5-7.

Figure 13:
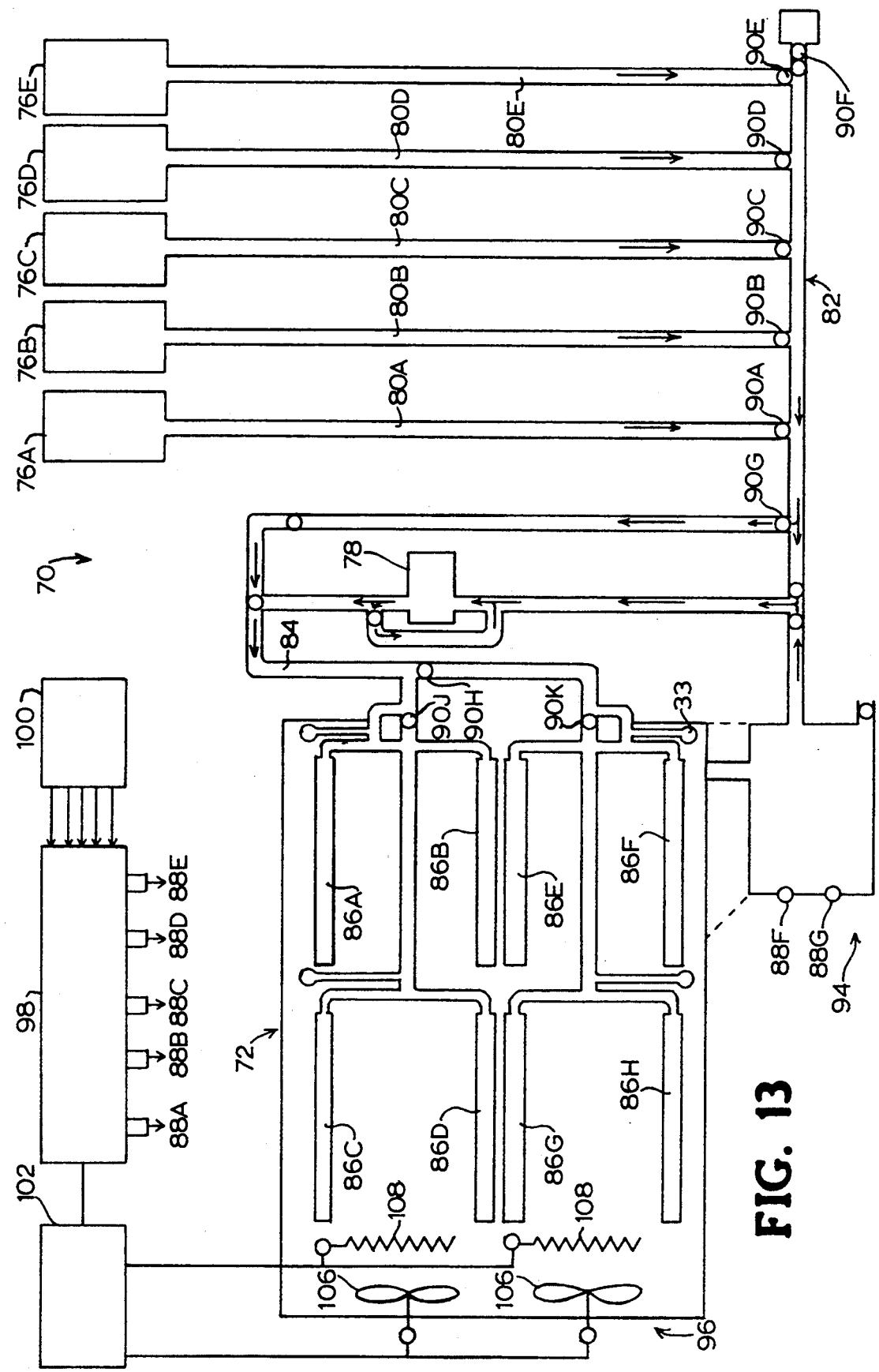
FIG. 13 is a schematic drawing of the automated gene identification apparatus of the invention.

The racks are also designed in such a way that they position the carrier for heating/cooling. An example of a heater (not shown) that might be used is a 2-dimensional resistant heater (Minco, Minneapolis, Minn.) laminated to an aluminum plate. Preferably aluminum fins are added as an extension of the aluminum plate to expand the heaters' heat-sinking capacity. The heater outputs are controlled by a programmable microprocessor and sensor inputs. The racks position the carriers in the instrument modules so that each carrier is at an intimate distance from a heated surface. Heat from the heater source 108 as shown in FIG. 13 is transferred to the matrix from the heater (not shown) whose surfaces closest to the racks may have protruding sections in a pattern that permits intimate contact with the carrier bottoms 16. An alternative heating method may be from resistance-type heating coils incorporated into specified locations in the rack. In either case, the intimate distance means that surfaces of the heater and carrier actually touch, or not, either continuously or intermittently, in a way that heat is convected through an air cushion layer from the protruding sections of the heat sink to the carrier or conducted from them or the rack directly to specific areas of the carrier bottom.

The heating system causes the matrix to attain a set point temperature (ramping) in a specified time period, maintain that temperature set point for a specified time period (soaking) and repeat throughout a programmed temperature profile. Temperature control in the matrix is necessary for providing conditions for the kinetics of specific biochemical reactions, i. e. specific enzyme activity or annealing or disassociation of complementary nucleic acids.

The uniqueness of this system is that all components are designed for augmenting the heat flow to the desired region and thus eliminates the need for refrigerated cooling for quickly lowering temperature. Rapid cooling of the matrix is achieved in the carrier by stopping current to heater just before set point is achieved or soak time is completed, and using the thermal mass of the carrier and matrix and all supporting structures, including the racks, to slow down heat conduction and convection and reverse it so heat flows away from the matrix/carrier in the direction of the larger thermal mass of the fins. The air cushion layer is the space between the plane of the heated surface and the plane of the carrier bottom 16 and preferably changes during the programmed temperature cycle. The air layer distance is determined for events in the system, and may be 0-2 cm, or somewhere in between at a particular point in the temperature cycling, in order to keep temperatures sufficiently consistent, one carrier to another, but large enough that the heat shift from conductive to convective mode (in the air cushion) causes a more rapid reverse flow than occurs if the surfaces were in tight and constant contact.

Figure 15:
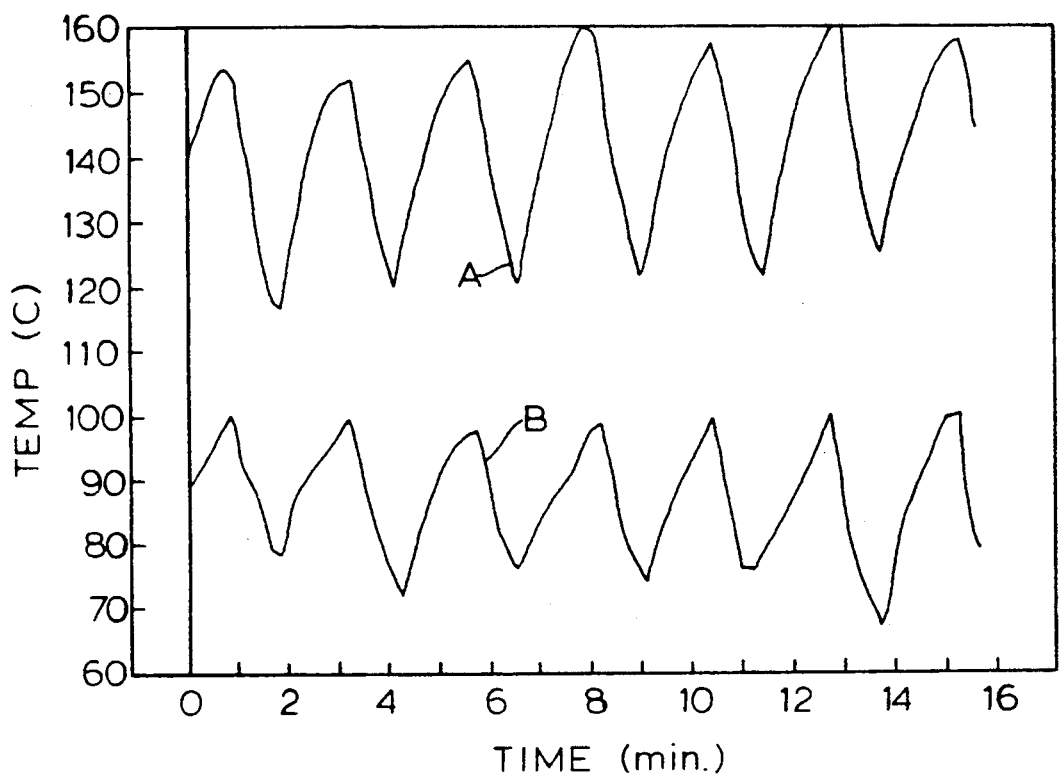
FIG. 15 represents temperature profiles in which thermal cycling such as that used for PCR is attained in the matrix.

Data is presented in FIG. 15 that show the differences in the measured temperatures of sensors on the heated surface (line A) and sensors on the carrier (line B) that provide typical thermal cycles. An increase in the width of the air cushion or intimate distance increases the slope of the cooling curve. The rack is the device which adjusts the width of the air cushion and thus contributes to temperature flow. What the coordination of current, distance and thermal mass of individual components accomplishes is thermal cycling for efficient, repetitive nucleic acid polymerization and denaturation without application of active cooling of other known means.

Extensive monitoring of temperature was accomplished with multiple sensors and PC data acquisition interface in order to analyze and establish the value of an air cushion and the working distances between heated surface and carrier, the watts per square inch capacity of the heated surface, the voltage necessary to heat the surface in the desired ramp time and the optimal temperature differential between the surfaces which bounded the air cushion. The temperature profiles in FIG. 15 are representative samples of the data which was collected and analyzed to determine the linear distance and temperature differential between the heated surface and positions on the carrier surface. Thus the carrier and rack become integral components in thermal cycling required for the biochemical processes in detecting nucleic acids.

The design of racks in which electrophoresis is used will position the matrix in such a way that the matrix completes an electrical circuit. This optional feature, that may be incorporated into the automated system for use of the instant invention, is the positioning of electrodes on each rack of a plurality of racks holding the matrix carriers of the type shown in FIG. 5–7, in such a way that applied current can pass through each matrix saturated with an electrical conducting buffer. Positive and negative connections are located on opposite ends of each matrix and connected via contact leads to positive and negative terminal blocks on the rack.

Figure 16:
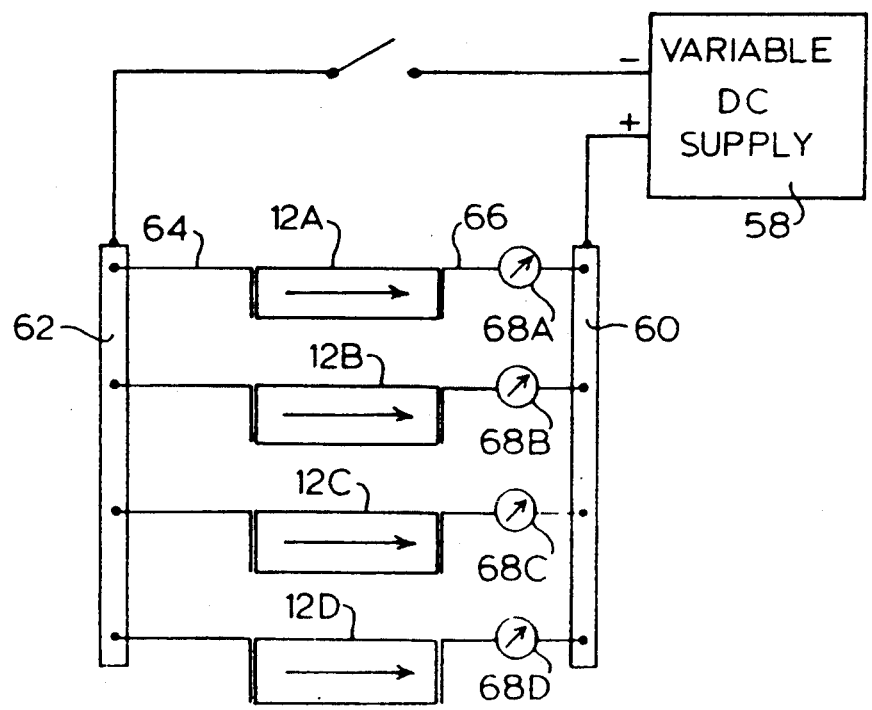
FIG. 16 is a schematic drawing of an electrical circuit closed by a matrix.
Figure 9:
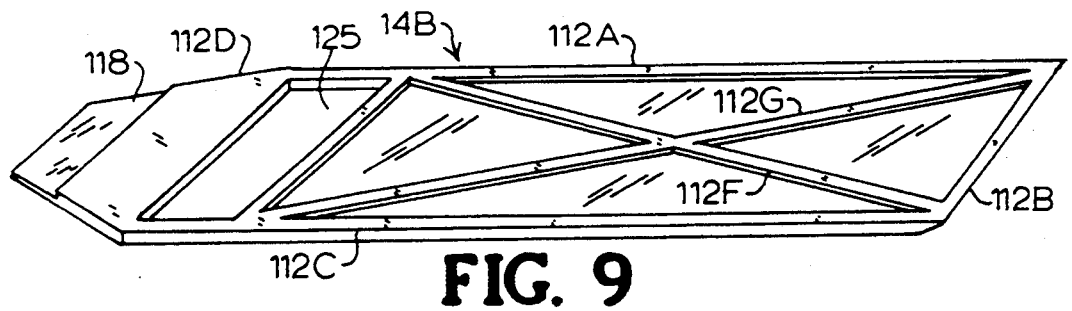
FIG. 9 is perspective drawing of a cover for use with the snap-on base of FIG. 8.
Figure 8:
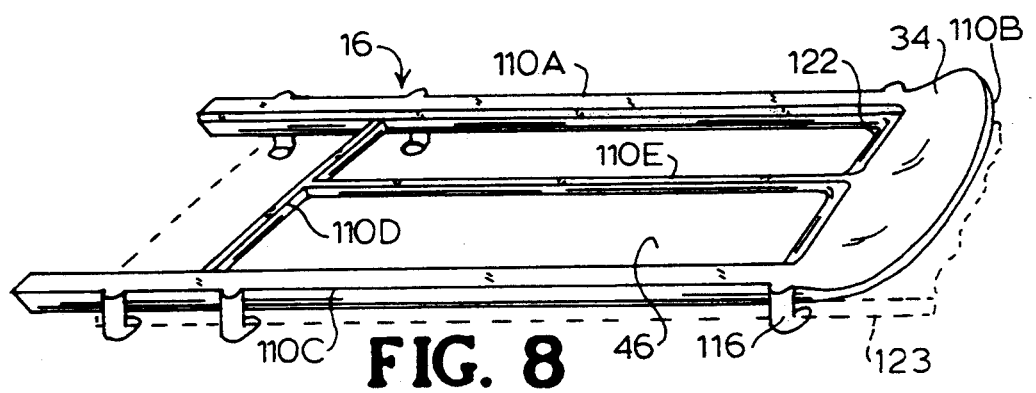
FIG. 8 is a perspective drawing of a third embodiment of the carrier showing a base that snaps onto standard microscope slides.

In reference to FIG. 16, a variable DC supply 58 has its positive side connected to an anode bus bar 60 and its negative side connected to a cathode bus bar 62. Each electrophoretic matrix 12 of which four are illustrated by way of example, labelled 12A, 12B, 12C, and 12D, is connected on one side to bus bar 62 by way of a lead 64 and on the opposite side to bus bar 60 by way of a lead 66. An ammeter 68 is placed in series with each matrix 12 as illustrated.

In use, the variable DC supply 58 as adjusted to provide an appropriate level of DC voltage and individual monitoring of the current through each matrix 12A, 12B, 12C, or 12D is obtained by monitoring the respective ammeters 68A, 68B, 68C, and 68D. Voltage levels are maintained at levels commonly used for electrophoresis. The ammeter can be connected to an alarm (not shown) so the operator may know if the electrical current is too high, as a backup to discover any inadequate matrices, where the resistance has increased more than in other matrices.

The rack has electrical connections 132 fitting into corresponding connections in the instrument when the racks are in position in the instrument. The rack terminal bus bar is thus connected to a power supply in the automated instrument. The invention so equipped will provide an equivalent electrical current through all gel matrices. In such racks electrical connections from the anode bus bar and cathode bus bar lead to each individual matrix-carrier 10, an anode to one end of the matrix and a cathode to its opposite end. Electrical wire connections are appropriately sheathed with insulating material where no current conductance is desired. Interlocks and lid locks will be placed at all points where an operator may inadvertently come into contact with the electric field.

The air flow system built into the thermal chamber is also used to cool the matrix carriers during electrophoresis and prevent uneven heat build-up. The closed position of the carriers during electrophoresis prevents evaporative loss of buffer from the matrices. The fluid-flow line 32 delivers buffers to the channels 34 to diffuse into the matrices as needed for saturating or cooling them.

Figure 14:
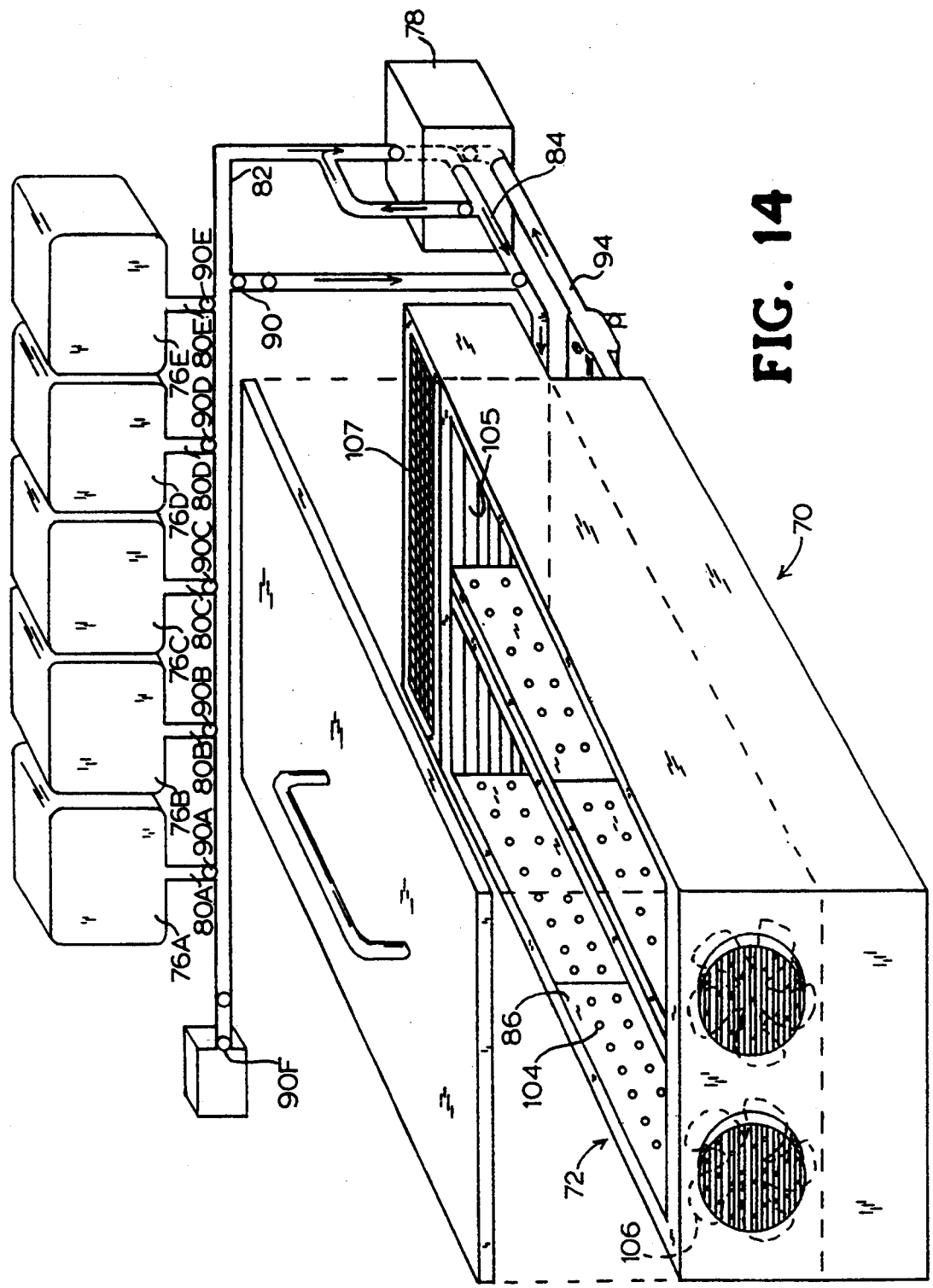
FIG. 14 is a perspective drawing of the overall gene identification apparatus embodying the invention.

Turning to FIGS. 13–14, the detection system 70 for detecting nucleic acid targets broadly comprises a reaction chamber 72 (FIGS. 13–14) in which samples, individually embedded in matrices 12 within carriers 10, are stacked in removable tray-racks 74 (FIG. 12) placed in the reaction chamber 72; a plurality of reservoirs 76 (FIGS. 13–14), each containing a solution or reagent for preparing the sample and promoting the detection of the target nucleic acid sequence; a pump 78 for transferring the solutions and reagents from the reservoirs 76 through secondary transfer lines 80, the supply manifold 82, and the main transfer line 84 to the jet spray manifolds 86 from which these fluids are sprayed into the reaction chamber 72; a system of switches 88A–88G, (and other switches not shown) and valves 90A–90K for regulating the flow of fluids; a drain system 94 for removing solutions and reagents from the reaction chamber 72; an air-flow system 96 that forces temperature-regulated air over the matrices 12 for drying and temperature control; a central microprocessor 98 which controls operation of the various components of the detection system 70; various sensors 100 and a power supply 102.

The reaction chamber 72 consists of several jet-spray manifolds 86A–86H (FIG. 13). One side of each manifold 86, facing a tray-rack 74, has openings 104 through which liquids are sprayed over the matrices 12. The size, arrangement and number of openings 104 are designed to maximize a rapid, uniform flow of solutions over the upper surface of the matrices 12.

In the preferred embodiment, reservoir 76A contains a lysing and denaturing solution; reservoir 76B, a neutralizing solution; reservoir 76C, the reagents for amplification; reservoir 76D, the reagents for hybridization; and reservoir 76E, a hybridization wash solution. Thus, in a similar way, each treatment solution is sprayed over the matrices sequentially. A particular reservoir's contents can be changed for each detection system so that custom-made primers (for amplification) and labeled probes (for hybridization detection) can be made for any known target nucleic acid nucleotide sequence. If different tray-rack loads are being treated for different target sequences in the same operation, an optional system of mini-reservoirs 33 may be made available to add different primer probes to each manifold section.

Drying cycles and water rinses are programmed between solution treatment sequences as necessary.

The drying cycle serves to prepare the samples for enhanced uptake of subsequent solution treatments. A drying cycle is initiated by actuating fans 106 and heating elements 108 to force heated air horizontally through the shelves of the tray-racks 74 around the matrices 12. The air-flow assists evaporation of moisture around the matrices 12 and actual dehydration of the matrices. The side of the reaction chamber 72 opposite the blowers has vents 105 so air flows into a closed chamber. The air escape is covered by filters 107 to contain any airborne biological components released from the samples.

The switches for the fans and heating elements actuate and deactuate them separately to provide for different set temperatures in different phases of the dehydrating, amplifying or hybridizing cycles. Thermocouples (not shown) at strategic locations in the reaction chamber 72 sense a representative matrix temperature and transmit this signal to the microprocessor 98. As programmed, the microprocessor activates heating elements 108 as necessary to maintain the upper temperature at the desired setpoint for each stage of the molecular processing. The fans 106 can produce air flow when heating elements 108 are deactuated to lower matrix temperature quickly. Solutions in the liquid cycle, which are normally cooler than the maximum matrix temperature (for denaturation), may be sprayed over the matrices to accomplish quick lowering of temperature. The binding of primers and probes requires prior melting of double-stranded DNA (dsDNA). This can be done by either a 95-degree C. temperature or an alkaline buffer. The coordination of components in both the fluid and air-flow cycles provides the temperature control needed for the molecular processes in the detection system 70.

A mechanical (for example, robotic) arm may be equipped with an auxiliary fluid line for delivering and dispensing reagents or solutions to the matrix carrier different from those supplied through fluid lines 32. A robotic arm may be used to apply precise volumes of particular reagents sequentially to each carrier's receiving area. This method of fluid delivery is in addition to the system which supplies fluids to all carriers simultaneously through the fluid line(s) described herein as 32.

The same mechanical arm may be so equipped with a scanning device to read all or a portion of the optical differences on the matrix surface. The purpose of the scanner is convert image data from the matrix to a digital form for computer interface. Scanning identification signals is incorporated into the final stage. The tray rack assembly exposes the flat surface of each matrix to a scanner, which reads the signals. The location and number of original target molecules present in the sample are reported by the signal. The scanning apparatus is interfaced with the microprocessor to give quantitative (location of signal) and qualitative (strength of signal) measurements. A representation of signal measurements made in situ may be printed out. Either the mechanical arm may move between the rack shelves or the rack may move past the mechanical arm. Scanner input data entered into a microprecessor matches the sample number with the identity of the sample and is further processed to determine the profile of the total sampled population. Software for the processor enables raw data of the sample to be structured with other information on the sample source and compared to a database.

With the invention, targets are spread at random in a manner analogous to spreading bacterial cells in nutrient agar and multiplying them "in situ", each colony becoming visible without microscopy and countable, if sufficiently spread, and each theoretically representing an original bacterium. In the spread sample or tissue section, with matrix "in situ" hybridization/amplification (MISHA) the nucleic acid target may be amplified "in situ" so that individual original copies become detectable by molecular means other than microscopy which is necessary for current/prior "in situ" hybridizations. The invention does not preclude microscopic analysis and morphological characterization of the sample either by one skilled in the art or by sophisticated image analysis systems. With the invention, the number of targets can be analyzed by less sophisticated image analysis systems and thus be valuable either as cost-effective prescreening of specimens for genetic sequences, or diagnosing an "active versus latent" disease stage or "pathological versus non-pathological" disease state.

In the following examples, amplification is defined as a means to biochemically increase the target nucleic acid mass. Target nucleic acid means those molecules containing a designated genetic sequence. Separation of nucleic acids by size utilizing electrophoresis is performed in a hydrogel supplied with an electrical current. Hybridization refers to the binding of complementary nucleic acids sequences, one partner of which carries a label whose signal can be detected. If amplification is used alone or follows hybridization it is understood that the primers or sequences used in binding targets or nucleotides for amplification may also carry a label.

It is understood that automated processing begins with sample preparation and ends with the test results of detection. It is further understood that standard reagents and reaction conditions may be used for the various sample treatment steps, such as amplification, electrophoresis and hybridization. The following examples are presented to iterate the ways in which the methods that are diagnostic of nucleic acid sequence-specificity may be interchanged or combined in the processing. In the following examples, the specimens in sections 46 are combined with matrix material which might be agarose; sections 54 are pre-formed in the carrier and may be different compositions to amplify different targets. Polymerase chain reaction (PCR) is shown as the preferred method of amplification using thermal cycling, but amplification is not limited to PCR or to thermal cycling because isothermal methods are known. Our research demonstrated amplification in agarose gels by PCR with Taq polymerase. The addition of more primer molecules during PCR as they are used retards formation of undesirable primer dimers. Although not discussed in detail herein, standard techniques including immuno-staining for analysis of polypeptides or other cellular components in gels may be performed with the device of the invention.

The features and advantages of the present invention will be more clearly understood by reference to the following examples, which are not to be construed as limiting the invention.

Example 1: Instrument Operation

To enable one to appreciate the value of the automated technology, the following is an example of what activities may be required of the healthcare worker or instrument operator depending on the circumstances.

(A) Add an aliquot of patient plasma to the carrier, add vial of matrix liquid to the carrier, and allow matrix to solidify. Load the carriers into the tray rack. Load the tray rack into the main chamber.

(B) Check instrument for signal indicating reservoirs are filled or need filling with the proper reagents.

(C) Select the proper test panel on the computer and follow computer instructions for checking or inserting cassette dispensers of enzyme solutions or labeled probe hybridization solutions specific for this test panel.

(D) Change program parameters if so desired.

(E) Start operation.

(F) Remove trays, remove carriers from tray and store.

(G) Access test results from the computer.

Example 2: Amplification

Amplification that is specific enough for detection without hybridization or electrophoresis is possible. Detection is by measuring the increase in mass of DNA or RNA after amplification. In this case measuring labeled nucleotide incorporation simplifies the assay. Unincorporated, labeled nucleotides may be readily washed away before detection.

Additionally, the more primer sequences used in PCR to amplify more fragments, the more specific is identification of target DNA. There is a dampening effect that limits the number of primer pairs that can be used together, which varies according to the nature of the target and background DNA or RNA. A particular assay may be used in which multiple primer pairs are used to increase the total quantity of DNA in the sample. Duplicate samples are run in parallel on the same matrix as positive and negative controls. The positive controls have primers to amplify a conserved region of specimen DNA that is species-specific and indicates the starting amount of total DNA present in the specimen. Another positive control of known target DNA demonstrates adequate assay conditions. A negative control starts with non-target DNA to indicate possible contamination of assays components.

Specimens that lack primer-binding targets do not increase DNA content and such a test is useful in genetic disease or tumors where deletions of both normal alleles cause a disease state. This test design may also be used to compare the number of copies of a tumorigenic or an oncogenic region with those of a single copy gene in order to quantify the extent to which the gene has been amplified naturally in any given tumor.

To enable one skilled the art to thoroughly appreciate and practice in detail the technique of the present invention, an amplification protocol and results are herewith provided:

1. CaSki (ATCC CRL 1550) and MRC-5 cells (ATCC CCL 171) are cultured and frozen using standard tissue culture techniques. A volume of thawed cells in culture fluid is mixed with a low concentration agarose solution in the sol phase and added to the carrier where gelation of the agarose matrix occurs.

2. The carriers are placed in the apparatus and the cells are treated with standard reagents for sample preparation, except that the cell treatment occurs in the matrix. The treatment consists of Pronase (1 mg/ml) and Triton-X (0.1%) in a Tris-buffered solution applied for a brief incubation period at 37° C.

3. The treatment solution is washed from the matrices with distilled water using the washing layer for diffusion as previously described. With the carrier open the matrix dehydrates quickly.

4. Amplification in the cells is detected by substituting digoxigenin-11-dUTP (Boehringer Mannhelm) 50:50 for the dTTP in a standard PCR reaction mix (Perkin-Elmer Cetus) and thermal cycling in the device of the invention through 25 cycles between 72° and 98° C. 25 times. The primers added to the PCR kit are specific for the E5 region of human papillomavirus, which is known to be integrated into the CaSki cell genome.

5. The incorporation of digoxigenin is detected by means of antibody conjugate and substrates (Genius TM DNA Detection Kit, Boehringer Mannheim).

Figure 18:
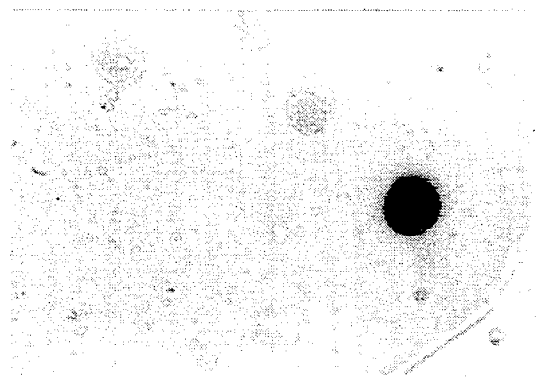
FIG. 18 illustrates a microscopic view of cells in the matrix after amplification and detection of a specific sequence in the cells while embedded in the matrix of a carrier and processed in the invention.

6. The carriers are microscopically photographed under the 30X objective with a Nikon camera as illustrated in FIG. 18. Deflection of incorporated nucleotides indicates that a polymerase chain reaction (PCR) is performed in cells embedded in the matrix in the device of the invention.

This example demonstrates that the process claimed may be used as a diagnostic by detecting an identifying genetic entity in cells. Counterstaining the matrix makes microscopic distinction between positive and negative cells. The two-dimensional format has the advantage of enumerating the percentage or proportion of the specimens cells with positive results.

A logical extension of this example is to use the device of the invention for an "in matrix" incubation period, wherein the biological entities or biological entities absorbed to co-culture cells replicate in the matrix at the sites in which they were individually immobilized. In so doing the assay may become a combined propagation, first of organisms, and then of molecular targets, in the same device.

It is understood that the amount of target nucleic acid may not be known if the process herein is used for diagnostic applications, so that the extent of amplification necessary for detection has to be estimated according to the specimen amount and type and the thresholds of target copies anticipated to be diagnostic for manifestations of the presence and/or quantity of the given genetic entity in the biological material. The sensitivity of detection is affected by the spreading of amplified target nucleic acids. It is obvious that the object of the invention is not to retain amplification targets at their site of synthesis, but make the matrix a scaffold so that amplified molecules spread enough from their templates for further amplification. Clusters are formed that may be distinguished as separate positive signals. However, if the detection signal such as chromogenic precipitate is such that one cluster may not be distinguished from another, the overall intensity may be measured by the same means. Experiments show that the intensity of signal increases with more amplification as would be expected. In experiments using agarose as a matrix material and plasmid DNA with the process and device herein, the ability to distinguish individual, positional amplification of original targets diminished as the number of amplification cycles increased when using thermal cycling which was likely due to increased diffusion of molecules during the brief phase transition of agarose from gel to sol at the denaturation temperature. This affect was not observed when cellular material was used as cells nor would it affect semi-quantitative measurements using sample dilutions. A logical outgrowth of these observations would be to find a matrix material that did not have a sol phase at the denaturation temperature of nucleic acids or use an isothermal amplification protocol.

Experiments testing the loading capacity of the matrix material to retain small, amplified fragments had a propitious result in that relatively few counts were lost in waste fluids from the washing layer. Tracking the small, labeled molecules indicated a significant quantity bound to the carrier surface adjacent to the position in the matrix where they were amplified, having little effect on the sensitivity of detection. This discovery leads to further claims that the device of the invention may serve to trap amplification products diffusing from the matrix on the carrier surface for detection. The binding character of the carrier can be controlled to bind or not bind selected molecules.

Example 3: Matrix and Carrier Design for Sample Preparation, Amplification and Hybridization The initial process of sample collection involves randomly distributing specimen in diluent if the sample is too concentrated for analysis, and then combining it with a liquid matrix material or a pre-formed matrix in the carrier.

The order of treatment methods in this example are sample preparation, amplification, hybridization and detection. This application would be used in a diagnostic in which amplification with specific primers yields discrete products from non-target DNA, some of which may even be in the same size class as the target DNA. These products can be discriminated by hybridization from target sequences. In particular, this protocol may be used for detecting proviral sequences of human immunodeficiency virus type 1 or human T-cell leukemia virus type 1 where these other products have been reported (Abbott, M. A., B. J. Poiesz, B.C. Byrne, S. Kwok, J. J. Sninsky and G. D. Ehrlich. 1988. Enzymatic gene amplification: qualitative and quantitative methods for detecting proviral DNA amplified in vitro. J. Inf. Dis. 158:1158–1169.).

If the specimen is a sample from blood or another body fluid, a measured amount may be added directly to the matrix 12 through the channel 34. The matrix carrier 10 is processed by heat or chemicals to embed the specimen in the matrix 12 and render it non-infectious. The matrix carrier 10 is closed during transfer to the instrument site, where it is loaded, along with others, onto a rack and placed in the thermal chamber of the instrument. The fluid delivery system sequentially supplies multiple reagents in series through an individual fluid line 32 to each matrix-carrier. Thus, a lysing-sample preparation solution from the fluid line 32 flows into the channel 34 on carrier section 16 and diffuses into the matrix 12 and is used to remove non-nucleic acid components in the sample. The carrier is mechanically opened as the solution reduces surface tension between the upper matrix surface and the carrier piece. The final solution of sample preparation rinses away previous solutions and forced, heated air of the thermal chamber dries the matrix with the carrier still open or the matrix is heated by conduction from heaters in the racks either contacting the carrier directly or positioned near it to generate a layer of heated air between heater surface and carrier.

The amplification solution and reagents are then added through the fluid line 32 to rehydrate the matrix. The carrier closes during amplification temperature cycling to prevent evaporation. A prototype resistance heater, rack and carriers in our possession have provided temperature cycling as specified for PCR. After amplification the carrier may open to facilitate rinsing and adding hybridization solutions. The carrier closes during hybridization to an enzymatically-labeled nucleotide probe and may open again for the stringency washes, and subsequent addition of substrate and buffers for detection. After substrate development the carrier closes for reading by a scanning detector. One possible detector may be an optical array for measuring transmitted or reflected light differences that distinguish positive signals over background noise. The scanning is not limited to detecting enzymatic activity on a chromogenic substrate, but other labels, such as fluorescence may be used.

Data from amplification and hybridization experiments with the matrix covered and uncovered indicate opening and closing of the carrier is critical to facilitate either rinsing or drying of the matrix in the open configuration and controlling evaporative loss during reaction periods in the closed position. Experiments which were performed in a covered or closed matrix had retarded diffusion of treatment solutions, and retarded rinsing and drying the matrix when the matrix touched the top piece of the carrier; however, shrinkage of the matrix (caused by the fact that it does not rehydrate to its original volume after drying) forms a space between the matrix surface and the upper piece 16. Solutions flowing through this space create the diffusion zone for effective diffusion in the closed position. A closed carrier prevents water evaporation from the matrix, thereby maintaining desired molar concentrations for periods of optimal enzyme activity and preventing increased signal noise that occurs when unwanted reagents molecules are fixed by drying in the matrix. The matrix capacity to absorb solutions is reduced after its first drying, thereby concentrating nucleic acids in a smaller volume of matrix and requiring fewer primer or probe molecules to maintain adequate molarity. Residual enzymes such as proteases or nucleases can be inactivated by drying them in the structure of the matrix so they will not be a problem in subsequent steps. A dried agarose matrix soaks up reagents like a sponge, hastening diffusion of necessary biomolecules added after a drying step. Drying and rehydrating the matrix has useful functions and the ability to open and close during processing as allowed by the carrier of the invention has been found to serve the above multiple purposes.

The spreading and embedding of a specimen sample such as plasma in the matrix represents essentially a two-dimensional plane in which single targets can be multiplied by known means and detected as individual entities for quantifying the number of original targets or approximating the original number. The multiplication of target molecules in the vicinity of each original target molecule allows detection by known means such as non-isotopic enzymatically- or fluorescently- tagged molecules. The specific advantage of multiplication by one of the molecular amplification techniques in a thin matrix is the ability to automatically enumerate the original copy number of targets with less costly and less sophisticated image analysis systems than those necessary to characterize "unamplified" nucleic acid "in situ" hybridization to targets and with technology that does not require interpretation by someone skilled in the art.

In the case of a genetic disease caused by a single base mutation such as a majority of cases of cystic fibrosis, the purpose of a diagnostic is to determine the presence of mutant alleles either as homozygous or heterozygous genes. Here amplification of the target DNA or RNA means fewer specimen cells are needed. After sample preparation and amplification, hybridization with the appropriate labeled oligonucleotide probes, under stringency conditions which distinguish either the single base-pair match or mismatch, will be sufficient for detecting a mutation related to the disease or carrier state.

Example 4: Matrix Carrier Design for Sample Preparation, Amplification and Electrophoretic Separation In this example, the sequence of methods is sample preparation, amplification, electrophoretic separation of amplified fragments, and detection by staining of fragments and scanning resulting bands for interpretation by image analysis software. This example illustrates the value of matrix subsections and racks designed with electrical bus bars leading to each matrix.

Figure 7:
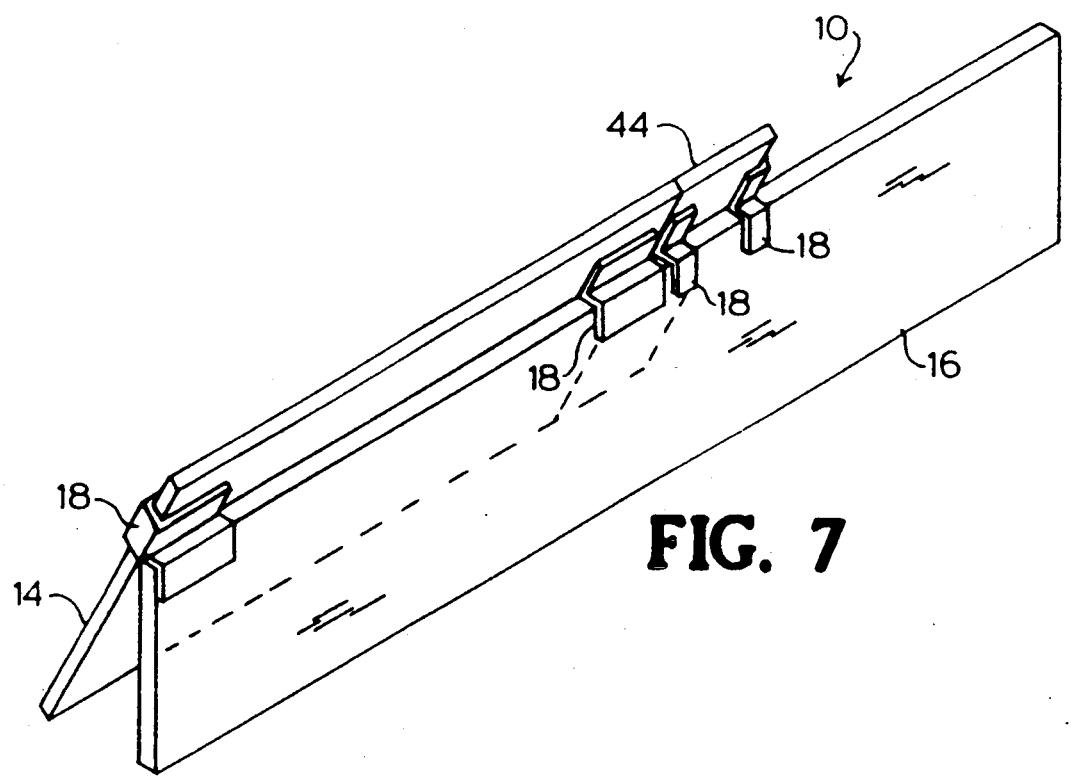
FIG. 7 is a back perspective view of the second embodiment of the invention showing the hinge.

An example of a subdivided matrix is illustrated in FIGS. 5–7. A mixture of specimen and matrix material is added to form subsections 46 of matrix 12. Although three subsections are shown, this amount maybe varied for particular uses. The fluid lines 32 are supplied by the fluid delivery system of the instrument. Carrier extension piece 44 is raised after the matrix and specimen subsections are set. Sections 46 are treated with fluids from fluid line 32 in order to make nucleic acids from particles/cells in the specimen more available for modification or detection and to reduce interference from non-nucleic acid molecules. The hinged edge of extension piece 44 has an opening(s) in order for fluids collecting around subsections 46 to drain off into troughs on the racks.

The contents of sections 54 and 56 are protected between the carrier halves 14 and 16 in the closed position or by the barriers formed by edge extensions 44. The treatment solutions from the fluid line 32, used for lysing and washing the sample, do not enter the enclosed sections 54 and 56. After sample preparation is complete in subsections 46, the instrument automatically opens the carrier enabling fluid to enter matrix sections 54 and 56. This fluid is an ionic buffer that permits DNA to migrate towards the anode when current is applied.

Current is supplied from leads from the bus bar fastened to the shelves of the rack in such a way that each matrix placed on the rack comes into electrical contact with leads of opposite polarity, and when saturated and current is applied, the matrices close parallel circuits. An electrical current flowing through the buffer-saturated matrix-coated carrier, as shown by the arrows on FIG. 16, causes the nucleic acids from the specimen in sub-sections 46 to migrate into subsections 54.

Preformed matrix subsections 54 may hold different primer sets for amplification of different target fragments in duplicate specimens, or a subsection 54 may contain known DNA standards. These designated primer sets could be immobilized in sections 54 at the time of matrix-carrier manufacture. After the first electrophoresis, the fluid line 32 supplies sections 54 with amplification buffers to supplement what reagents are already incorporated in them. Controlled temperature cycles allow treatments from fluid line 32 to enzymatically amplify a specific target DNA sequence in closed carriers. The carrier may be sealed in manufacture with a polyethylene film to cover matrix sections 54 and 56 and prevent contact with aqueous fluids from channel 34. Once the carrier is opened, the seal is physically separated so that subsequent closing of the carrier allows fluids to be drawn through the carrier halves when closed.

The second application of current allows the DNA molecules, including the amplification products, to migrate into section 56. In cases where primers were reversibly immobilized in the preformed matrix subsections, a treatment step to release them is included. Section 56 is also a pre-formed matrix of still a different composition. The composition of section 56 is selected to resolve different-sized fragments; the composition and buffers chosen could be as described by Allen et al. (supra) comprising a 5% T wedge rehydrated polyacrylamide gel and discontinuous buffer system. In a discontinuous buffer system a sulfate-leading ion made by adding $H_2SO_4$ in a buffer may be incorporated into the cathodal end of the section 56 matrix and the borate-trailing ion incorporated into the overall section 56. The ions may be supplied by prior incorporation of one into the matrix section with the other supplied by fluid line 32 at the time of electrophoresis. In instances where ionic buffer salts are incorporated in the matrix 56, adding deionized water through fluid line 32 will sufficiently hydrate the matrix to supply the buffer requirements. In other instances buffer prepared at its final concentration is supplied through fluid line 32.

After the electrophoretic separation of DNA fragments, the carrier halves are opened to permit staining solutions to diffuse into section 56 and stain fragments for visualization. The fluid line 32 supplies staining solutions. DNA identification in this case results from comparing bands representing the electrophoretic mobility of an expected target fragment size-class to standards and/or other specimens. In this example all nucleic acids present in the matrix are stained and the preferred method of staining might be silver staining according to the modification of Allen et al. in which polymerase chain reaction amplification products are separated on rehydratable polyacrylamide gels and stained with silver which detects 10 pg/mm band widths (Allen, R. C., G. Graves and B. Budowle, BioTechniques 7:736–744, 1989). The staining process is developed to an optimal level. The carrier halves are closed after staining treatments to flatten the matrix in one plane for scanner reading. The ability to standardize the electrophoretic pattern by quality control production of carriers and matrices makes it easier to compile a database of a digitized form of a person's unique band pattern relative to controls, and enable searches for matching or related banding patterns automatically with the appropriate software. A database thus generated may better estimate the statistical chance that specific band patterns occur in defined subpopulations and thus be more appropriate interpretation of genetic specimens for identity purposes.

A mechanical arm passes the carrier half that is transparent by either movement of the arm or the rack. The mechanical arm might contain an arc light as a light source, lenses for focusing or intensifying light, and an optical array for detecting either transmitted or reflected light. The intensity of the light source and the speed of the pass can be varied to produce the best signal-to-noise ratio and be set to an internal standard matrix before reading the other matrices.

Examples 3 and 4 demonstrate the use of designated matrix carriers in the automated system, the first one being a viral diagnostic test and the second being a DNA identification test. A specialized carrier enables many functions to occur on an individual carrier which is processed automatically along with others in the same fashion. In the second example, closing the matrix halves is critical in protecting a matrix subsection during prior treatment to another subsection and opening is critical in permitting rehydration of a preformed matrix. The fluid delivery system supplies different reagents through a common fluid line to individual matrices. The common fluid line may carry multiple reagent supply lines so that there may be several openings at the end of the line, each opening dispensing a different fluid and being separately controlled. The DNA from the specimen in the second example migrates from one subsection of the matrix carrier to another by electrophoresis. Subsections 46 are thicker than 54 in order to prepare the sample in a larger matrix volume and then concentrate it by drying. Experiments performed with the carrier of the invention demonstrate that fragments will migrate through dried and rehydrated gels to other gel matrices. Fractionating the DNA in ultra-thin matrices results in better signal detection. The matrix subsections of the carrier of the invention have been found to serve the above multiple purposes.

Two matrix carrier designs are described above in detail to illustrate how different types of matrix carriers may be designed to fit the needs of particular DNA-based tests. The following examples are described very briefly to enumerate possible combinations that exist for additional matrix carrier designs.

The automated system as outlined in each of the examples includes sample preparation as the first step and detection (reading and interpreting signal) as the final step. The intermediate steps are defined as those which supply the specificity of nucleic acid sequence to the system and vary among the examples.

Example 5: Amplification, Electrophoretic Separation and Hybridization

A variation of Example 4 may be used when electrophoretic band patterns of amplified fragments are ambiguous. Rather than staining all DNA bands for detection as illustrated in Example 4, hybridization with labeled probes permits detection of only those bands having sequence complementarity.

Example 6: Amplification, Hybridization and Electrophoretic Separation

A variation of Example 5, in which the order of electrophoresis and hybridization are reversed, may be used when detection of amplification products is improved by electrophoresis after labeled molecular probes have bound to them. The DNA product-labeled probe complex may have a more distinguishable electrophoretic band pattern. Another advantage is that hybridization is more efficient in the smaller volume of a matrix subsection than it is in the volume of a larger matrix section into which DNA has been electrophoresed.

Example 7: Hybridization

If in Example 3, sufficient components are present in a specimen, amplification may not be required and the detection would require only hybridization to a labeled probe after sample preparation. The ability to infuse a tissue specimen (by way of example, prepared thin sections or smears of exfoliated cells) with a matrix material has been shown to improve the accessibility of target nucleic acids, preservation of tissue morphology and the ability of labeled probes to hybridize to these targets. The addition of a matrix material in the carrier-holding area with tissue for "in situ" hybridization preparations is termed herein Matrix In Situ Hybridization (MISH).

Example 8: Hybridization and Electrophoretic Separation

One instance where hybridization followed by electrophoresis would be useful is where labeled DNA probes are hybridized to RNA transcripts and the DNA:RNA hybrids produce a fragment size class distinguishable by electrophoresis. Similarly, labeled DNA or RNA complexes may be cleaved at particular recognition sites and electrophoresed to enhance their detection.

Example 9: Hybridization, Electrophoretic Separation and Amplification

If in Example 8, the amount of target is below detectable levels, amplification increases sensitivity of detection and may be performed after hybridization and electrophoresis.

Example 10: Hybridization and Amplification

The Q-beta replicase method of detection is an example of hybridization before amplification and may be used in the device of the invention. (Lizardi, P.M., C. E. Guerra, H. Lomeli, I. Tussie-Lune, F. R. Kramer. 1988. Exponential Amplification of Recombinant-RNA Hybridization Probes. Biotechnol. 6:1197–1202.) An oligonucleotide probe is inserted in a RNA that serves as a template for RNA synthesis by the enzyme called Q-beta replicase. The enzyme polymerizes multiple RNA transcripts which include the target sequence.

Example 11: Hybridization, Amplification and Electrophoretic Separation

Electrophoretic separation after RNA transcripts are produced according to Example 10 or by other means is a way to analyze the integrity of the RNA transcripts. The mobility of the RNA provides verification that the relatively large mass of RNA generated is in the size class of desired recombinant RNA.

Example 12: Electrophoretic Separation and Hybridization

Restriction Fragment Length Polymorphisms (RFLPs) are DNA fragments resulting from endonuclease cleavage of genomic DNA whose length varies from individual to individual by virtue of whether the specific recognition site of the endonuclease is present or not at a given location in the genome. After electrophoretic separation of these fragments according to size class using the device of the invention, labeled DNA probes are hybridized to these variable regions resulting in unique banding patterns which identify an individual and the individual's relatedness to other individuals. In some instances the same genetic variation that alters the restriction site also causes an abnormal phenotype and thus determines the disease condition directly. In other instances, linkage relationships are established between a genetic defect and an RFLP allele which acts as a genetic marker. RFLP's are used to identify genetic diseases or predict chances that offspring will inherit a genetic disease. They may also be used to prove or disprove identity in paternity or forensic cases.

Example 13: Electrophoretic Separation

Electrophoretic separation in the device without amplification or hybridization may be sufficient to provide useful information. In less genetically complex organisms the electrophoretic banding pattern of endonuclease-restricted total genomic DNA yields strain or species identity. In bacteria, for example, a densitometric scan of these electrophoretic bands can distinguish one kind of bacteria from another.

Example 14: Electrophoretic Separation and Amplification

Amplification of a specific size class of the restricted DNA may be performed directly in the same hydrogel matrix in which the size classes have been separated in the device. In cases where more than species identification is necessary, electrophoresis first helps purify DNA from the total specimen. Then amplification before final DNA detection means that specificity of amplification is combined with specific electrophoretic mobility to make detection of signal stronger and thereby easier over background DNA.

Example 15: Electrophoretic Separation, Amplification, and Hybridization

Hybridizing a labeled nucleic acid probe to nucleic acid targets produced as according to Example 14 is a way to determine the presence of specific DNA targets, thus reducing matrix background signal and simplifying software interpretation of the results.

Example 16: Electrophoretic Separation, Hybridization, and Amplification

Initial electrophoresis of nucleic acids as in Examples 12–14 may be followed by hybridization with one or more primary molecular probes, which are then amplified by one of the transcription-based methods such as the Q Beta replicase method see Lizardi et al., cited in Example 10).

While the invention has been described in detail with respect to specific illustrative examples and embodiments, it will be apparent that numerous other variations, modifications, and embodiments are possible, and accordingly all such variations, modifications and embodiments are to be regarded as being within the spirit and scope of the invention. Such variations include, but are not limited to the detection of RNA or protein or other cellular components in the device using known detection methods and reagents.

BEST MODE FOR CARRYING OUT THE INVENTION

The molecular processing is accomplished by processor-controlled commands for the fluid/air flow reactor system which serves the molecular manipulations by providing the necessary microenvironment in the individual matrices. The command system for controlling the microenvironment is chosen for specific gene probe sequences or different types of specimens and consists primarily of duration, pH and temperature of treatments containing standard and custom-made solutions. A user of the system needs only to enter the desired program of treatments into the processor, connect appropriate reservoir bottles to the system, add samples to matrix liquid, load the samples into trays and the trays into the chamber. The processor then automatically selects predetermined appropriate reaction conditions (time, duration, treatment solution, solvent or reagent) for the sample type, and initiates the appropriate commands, in the appropriate sequence, and at the appropriate times to obtain matrix conditions which allow the molecular manipulations.

The carrier device of the invention is made to include a top piece and a bottom piece, said bottom piece having a matrix holding area, said top piece having a closed position; said top piece and said bottom piece hinged together along a first side of said bottom piece, said top piece having a first area that extends beyond said first side, whereby force causes the top piece to hingedly move away from the bottom piece and upward from the closed position to an open position; and said bottom piece having an overlap area on a second side of said bottom piece, said overlap area extending beyond said top piece, said overlap area having a fluid receiving depression, whereby fluid added to said fluid receiving depression may diffuse into matrix material placed in said matrix holding area exiting the washing layer (diffusion zone) opposite the entrance of the fluid.

Specimens are analyzed by placing a matrix material in the device, adding the specimen to the matrix material, and detecting and/or quantitating the desired component by processes which may include amplification, use of electric current and/or labelled probes.

INDUSTRIAL APPLICABILITY

Any biological sample or environmental sample suspected of containing biological material is considered a sample. Each sample is mixed with aliquots of liquid matrix and allowed to solidify. A batch of sample matrices is subjected to subsequent treatments automatically in the reaction chamber. Blood, plasma, saliva, cerebrospinal fluid, lymph, urine, homogenous tissue, cell cultures, viruses, water, and soil are examples of sample material, but the process is not limited to these materials. For in situ identification of nucleic acids, tissue sections (prepared by standard methods for microscopy) may be overlaid with liquid matrix placed on tray rack shelves and then treated as other matrices. These matrices may also be scanned microscopically to localize the presence of target nucleic acids in the tissue. Gels containing nucleic acid samples, prepared by standard methods and size-fractionated by gel electrophoresis, may be amplified further and/or hybridized in this system.

The system's flexible programming allows use of the device for research and clinical applications in which only one or two of the phases are required. Some examples of the different uses are preparation of large-sized DNA or intact chromosomes from cultured cells or organisms for other DNA manipulations, amplification of target DNA for other DNA manipulations, probe hybridization in gels in which nucleic acids have been size-fractionated by electrophoresis, or in situ amplification and hybridization of nucleic acids of tissue sections for microscopy. If the RNA in the sample is the target to be amplified, the sample is treated with reverse transcriptase to make a nucleic acid complement of the RNA just prior to the amplification step.

The ability to monitor specific nucleic acid sequences in biological material allows surveillance of genetic changes and fate-monitoring of known genetic changes. Both the lack of sensitivity of current probes and the labor-intensive preparation of the biological material has slowed application of recombinant DNA technology. The sensitivity of gene probes is increasing but some biological samples, especially those from the environment or a large population base, require massive sampling and screening to monitor the dispersal of the target gene. This method, which eliminates tedious sample preparation by automating the procedure, expands the ability to study gene competition, stability, dispersion and evaluate efficacy of new, recombinant DNA product treatments.

The device and method of the invention may be used to contain and transport specimens for automated processing to determine the presence and/or amount of a selected target component. Such processing is useful for example, in determination of the presence of viruses or biological components such as sequence-specific nucleic acids in fluids, or tissues of plants and animals, in microorganisms, or in environmental samples; the identity ("finger-printing") of an individual from the sample; the presence of genetic similarities, diseases, or abnormalities; or mapping of genes.

I claim:

1. An apparatus for automated liquid delivery to and precise temperature control of samples immobilized on a surface of a carrier device for the detection of genetic material comprising:
   (a) a reaction chamber for situating the samples, said samples individually immobilized in a thin, flat carrier device in said apparatus during treatments; said carrier device comprising a top piece and a bottom piece, said bottom piece having a specimen holding area, said top piece having a closed position; said top piece and said bottom piece hinged together along a first side of said bottom piece, said top piece having a first area that extends beyond said first side, wherein the top piece may be caused to hingedly move away from the bottom piece and upward from the closed position to an open position; and said bottom piece having an overlap area on a second side of said bottom piece, said overlap area extending beyond said top piece, said overlap area having a fluid receiving area; said reaction chamber containing a tray rack for holding a plurality of carrier devices;
   (b) reservoirs for treatment liquids;
   (c) treatment liquid transfer lines, said reservoirs connected to the reaction chamber by means of said treatment liquid transfer lines;
   (d) means to control the timing and volume of treatment liquids delivered to samples through liquid transfer lines; said carriers situated in said tray rack in a generally horizontal position so that liquids are dispensed sequentially into an end of each carrier and flow over said immobilized sample and the liquids exit the carrier at the end of the carrier opposite the end of the carrier where liquids are dispensed;
   (e) a pump to cause the treatment liquids to move through the treatment liquid transfer lines to the samples in the reaction chamber,
   (f) means to regulate and rapidly change temperature of the samples in said flat carrier devices in the reaction chamber; and
   (g) means to contain used treatment liquids away from the samples;
wherein liquid delivery and precise temperature control are controlled by a programmable central microprocessor.

2. An apparatus according to, claim 1, further comprising a thin, flat matrix in said carrier device selected from a group consisting of agarose, polyacrylamide, and mixtures thereof, with means to supply electric current to said matrix situated in each said carrier device positioned in said tray rack in a way that each said matrix completes an electrical circuit for electrophoresis.

3. A method for studying genetic material of a sample in comprising the steps of:
   (a) providing a thin, flat semi-solid gel matrix containing the sample in an apparatus comprising;
      (i) a reaction chamber containing a tray rack for holding a plurality of thin, flat samples;
      (ii) means to control the timing and volume of sequential treatment fluids delivered to each said sample;
      (iii) means to regulate and rapidly change temperature of each said
   (b) treating the samples immobilized in said gel matrix with treatment liquids in an amount effective to remove interfering, non-genetic material from the sample;
   (c) dehydrating the matrix to decrease volume of said matrix;
   (d) saturating the matrix with a first reagent;
   (e) denaturing the genetic material;
   (f) rapidly adjusting temperature for nucleic acid strand melting and annealing;
   (g) enzymatically amplifying the genetic material to be identified; wherein said amplifying is selected from a group consisting of polymerase and ligase techniques, and wherein specific, native nucleic acid sequences are used as templates repeatedly;
   (h) repeating steps (e) through (g) until a specific nucleic acid target is amplified sufficiently to be detected; and
   (i) rinsing away reagents and repeating steps (d) through (f) with appropriate reagents to detect specific genetic material within the matrix;
wherein steps (b) through (i) are done within the said apparatus.

4. A method for studying genetic material in a sample according to claim 3, further comprising spreading nucleic acid fragments in the said gel matrix by subjecting them to electrophoresis before step (e) of claim 3 or after step (h) of claim 3.

5. A process of specimen handling for analysis of a particular nucleic acid sequence of a specimen, comprising:
   (a) immobilizing a flat thin specimen in a specimen holding area in a carrier device, said carrier device comprising: a top piece and a bottom piece, said bottom piece having a specimen holding area, said top piece having a closed position; said top piece and said bottom piece hinged together along a first side of said bottom piece, said top piece having a first area that extends beyond said first side, wherein the top piece may be caused to hingedly move away from the bottom piece and upward from the closed position to an open position; and said bottom piece having an overlap area on a second side of said bottom piece, said overlap area extending beyond said top piece, said overlap area having a fluid receiving area; said carrier device in an apparatus comprising;
      (i) a reaction chamber containing a tray rack for holding a plurality of thin, flat specimens;
      (ii) means to control the timing and volume of sequential treatment fluids delivered to each of said specimens;
      (iii) means to regulate and rapidly change temperature of each of said specimens;
   (b) providing a zone for fluid entry to the specimen, contact of the fluid with the specimen and exit of waste fluid from the specimen;
   (c) alternately heating and cooling the carrier device to regulate specimen temperatures needed for nucleic acid strand denaturation, annealing of specific primers, and enzymatic amplification; and
   (d) processing the specimen by utilizing one or more of the following methods:

(i) amplifying in situ by primer extensions using a polymerase, wherein each specific, native nucleic acid target is repeatedly used as a template;
(ii) amplifying in situ by primer extensions using a polymerase, wherein each specific, native nucleic acid target and said primer extensions are repeatedly used as templates; and
(iii) amplifying in situ by binding oligonucleotide sequences to their specific target sequences so that the oligonucleotides are directly adjacent and repeatedly ligating said adjacent oligonucleotides;

wherein all processing of the specimen is preformed in the carrier device and wherein the presence and position of localized original nucleic acids targets in the specimen are distinguished and enumerated microscopically in situ.

* * * * *

UNITED STATES PATENT AND TRADEMARK OFFICE
CERTIFICATE OF CORRECTION

PATENT NO. : 5,451,500
DATED : September 19, 1995
INVENTOR(S) : Marilyn J. Stapleton It is certified that error appears in the above-indentified patent and that said Letters Patent is hereby corrected as shown below:

Column 22, line 20, replace "deflection" with --detection--

Column 29, line 10, replace "electrophoretlc" with --electrophoretic--

Claim 3, Column 31, line 64, add --situ-- after "in"

Claim 3, Column 32, line 5, add --sample-- after "said"

Signed and Sealed this

Fourteenth Day of May, 1996

Attest:

BRUCE LEHMAN

*Attesting Officer*   *Commissioner of Patents and Trademarks*